United States Patent
Musso et al.

(10) Patent No.: US 12,369,861 B2
(45) Date of Patent: Jul. 29, 2025

(54) METHODS, SYSTEMS, AND FRAMEWORKS FOR DEBIASING DATA IN DRUG DISCOVERY PREDICTIONS

(71) Applicant: BioSymetrics, Inc., New York, NY (US)

(72) Inventors: Gabriel Musso, Toronto (CA); Nishanth Merwin, Toronto (CA)

(73) Assignee: BIOSYMETRICS, INC., New York, NY (US)

( * ) Notice: Subject to any disclaimer, the term of this patent is extended or adjusted under 35 U.S.C. 154(b) by 0 days.

(21) Appl. No.: 18/058,732

(22) Filed: Nov. 23, 2022

(65) Prior Publication Data

US 2023/0389878 A1 Dec. 7, 2023

Related U.S. Application Data

(63) Continuation-in-part of application No. 17/831,571, filed on Jun. 3, 2022.

(51) Int. Cl.
*G06N 20/00* (2019.01)
*A61B 5/00* (2006.01)
*G06F 18/21* (2023.01)
*G06F 18/2135* (2023.01)

(52) U.S. Cl.
CPC .......... *A61B 5/7221* (2013.01); *A61B 5/7267* (2013.01); *G06F 18/2135* (2023.01); *G06F 18/217* (2023.01); *G06N 20/00* (2019.01)

(58) Field of Classification Search
CPC .... A61B 5/7221; A61B 5/7267; G06N 20/00; G06F 18/217; G06F 18/2135
See application file for complete search history.

(56) References Cited

U.S. PATENT DOCUMENTS

| | | | | |
|---|---|---|---|---|
| 2005/0141757 A1* | 6/2005 | Ayache | ........ | G06T 7/30 382/128 |
| 2013/0179375 A1* | 7/2013 | Tatonetti | ........ | G06N 20/00 706/12 |
| 2015/0106020 A1* | 4/2015 | Chung | ........ | G16H 40/67 702/19 |
| 2021/0158523 A1* | 5/2021 | Khademi | ........ | G01R 33/5608 |

* cited by examiner

*Primary Examiner* — Thai Q Tran
*Assistant Examiner* — Jose M Mesa
(74) *Attorney, Agent, or Firm* — LSIP Law LLC

(57) ABSTRACT

Some embodiments relate to methods, systems, and frameworks for data analytics using machine learning, such as methods and systems for preprocessing of biomedical data, using machine learning, for input to a predictive model. The method may include receiving data from a data source, using at least one machine learning (ML) algorithm from a plurality of ML algorithms to obtain at least one combination of preprocessing steps, and computing an accuracy score for each of the at least one combination based on accuracy of prediction of the predictive model. The method may further include using at least one ML algorithm to optimize the feature selection of the predictive model, combining a plurality of datasets into a single dataset, and using a parallel computing network to provide a framework for executing such predictive model.

9 Claims, 31 Drawing Sheets

METHODS, SYSTEMS, AND FRAMEWORKS FOR DEBIASING DATA IN DRUG DISCOVERY PREDICTIONS

BACKGROUND

Some embodiments generally relate to methods, systems, and frameworks for data analytics using machine learning. In particular, some embodiments relate to preprocessing biomedical data, using machine learning, such as for input to a predictive model.

The availability of biomedical data is at an all-time high due to breakthroughs made in the fields of genomics, proteomics, medical imaging, and wearable medical devices. For example, the cost of human genome sequencing has decreased tremendously from $3 billion in 2003 to $5,000 per genome in 2013. As a result, the approach for treatment of diseases has changed significantly to become heavily data driven. Data collection methods are becoming increasingly digital and automated. Precision medicine (a system for more personalized disease treatment) and robot-assisted surgeries are now a reality.

Breakthroughs have also been made in the fields of data science, machine learning, artificial intelligence, and computer processing. These fields have been applied successfully to automate the data analysis of large datasets, which are known as big data. In biomedical data too, these approaches have been applied successfully. However, the rapid increase in data has made it essential for the data processing technologies to keep evolving with the growth of big data. Efforts are also being made to improve the performance of such automated analysis in terms of speed of computation as well as accuracy of analysis.

Data pre-processing is one of the initial stages in a data analysis method involving making the raw data more consistent and transforming it into a form that can be used for optimized analytical outcomes. Data preprocessing often involves some computer programming and mathematics which a biomedical scientist may not have competency with. Feature selection is also a step in a data analysis method, involving selecting certain variables which directly impact the outcome of a model (for example diagnosis of a disease). However, in large dataset(s), with numerous variables, it may be a difficult procedure to execute. Integration of datasets leads to a larger set of variables may increase the reliability of predictions of a model. Optimizing the analysis of biomedical phenomenon (e.g., diagnostics, therapeutics, drug discovery, classifying different biological components), may require the use of different datasets along with distinct types of preprocessing and feature selection strategies so that the successful integration and analysis of the datasets may involve examining many different variables. Cloud-based as well as multi-processor equipped hardware allows for the execution of an algorithm in parallel over different Central Processing Units (CPUs) and/or Graphical Processing Units (GPUs) as well as Tensor Processing Units (developed by Google), Programmable Gate Arrays (PGAs), Digital Signal Processors (DSPs) and other processing technologies, leading to a higher computational capacity. Despite these innovations in computation, running different data pre-processing routings to achieve the best results often requires substantial computing resources which can consume substantial time and/or money when fee-based computation is used (e.g., with many fee-based or compute-usage based, cloud-based computing resources).

SUMMARY

It may therefore be advantageous to address one or more of the issues identified above, such as by using a system to automate and optimize a preprocessing algorithm in a predictive model. The (Machine Learning ML) algorithm allows for the selection of a suitable combination of preprocessing steps, with each of the preprocessing steps having suitable associated parameters, for a particular data type.

It may also be advantageous to address one or more of the issues identified above, such as by using an ML algorithm to obtain a plurality of features to successfully make use of a dataset. The ML algorithm tests each of the features of the dataset for their impact on the prediction accuracy and gives a set of relevant and optimized features for the predictive model.

It may also be advantageous to address one or more of the issues identified above, such as by combining a plurality of datasets of varying data types into a single dataset and using an ML algorithm to perform preprocessing and feature selection on the combined data set. The ML algorithm provides a means by which the evaluation of the various combinations of datasets and a set of features from the combined dataset can be conducted to optimize the predictive value of the data.

It may also be advantageous to address one or more of the issues identified above, such as by using a parallel computing network to run the preprocessing, feature selection, and data integration algorithms. The parallel computing network provides additional CPUs and/or GPUs and a framework for a plurality of users to work on the same dataset.

Some embodiments therefore provide methods and systems for preprocessing, feature selection and integration of data that may be deployed over a cloud network.

One such embodiment is a method for preprocessing biomedical data for a predictive model. The method includes receiving data from a data source. The method further includes using at least one ML algorithm from a plurality of ML algorithms to obtain at least one combination of preprocessing steps. The method further includes computing an accuracy score for each of the at least one combination(s) based on accuracy of prediction of the predictive model.

Another such embodiment is a preprocessing device for preprocessing biomedical data for a predictive model. The preprocessing device includes at least one processor and a computer-readable medium storing instruction that, when executed by the at least one processor, causes the at least one processor to perform operations. The device includes receiving data from a data source. The device further includes using at least one ML algorithm from a plurality of ML algorithms to obtain at least one combination of preprocessing steps. The device includes computing an accuracy score for each of the at least one combination(s) based on the accuracy of the prediction of the predictive model.

Yet another such embodiment is a method of selecting features from biomedical data for a predictive model. The method includes receiving data from a data source. The method further includes generating a number of features to be used for a predictive analysis of the data, wherein a feature is a random variable having an impact on an outcome of the predictive model. The method further includes iterating over a range of two numbers of features to select a suitable number of features for the predictive model. The method further includes using a transformation algorithm to convert the selected features into different mathematical functions of the selected features.

Yet another such embodiment is a method of combining a plurality of biomedical datasets for a predictive model. The method includes receiving a query from a user for a plurality of datasets to be combined. The method further includes receiving the plurality datasets to be combined from at least one data source. The method further includes combining the plurality of datasets.

Yet another embodiment is a method of using a computing network to run a predictive model for biomedical data. The method includes receiving data from a data source through an Application Programming Interface (API), wherein the API is a framework to allow the parallel computing network access to the data source. The method further includes storing a part of the data received from the data source through the API as a cache memory. The method further includes storing a list of a plurality of tasks in a task queue, wherein the plurality of tasks is performed in the background of the parallel computing network. The method further includes allowing a plurality of users to work together on the data. The method further includes distributing a plurality of algorithms over a plurality of CPUs.

The techniques of the above embodiments provide for an ML framework for analyzing biomedical data using a predictive model. The techniques may use ML itself for optimizing each step of the predictive model. The techniques further seek to reduce the compute resource, in particular, processor utilization, thereby making the process of data analytics compatible with cost-structure which is frequently associated with cloud-based computing. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Exemplary embodiments are described with reference to the accompanying drawings. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

(1) Summaries of Various Embodiments

One or more embodiments of preprocessing biomedical data for a predictive model are disclosed. The one or more embodiments provide for an ML framework for analyzing biomedical data using a predictive model. The one or more embodiments make use of the various components including preprocessing, feature selection, data integration, and parallel computing network.

(1.1) Preprocessing

Preprocessing is a method for preparing data, in its raw form, for further data analysis in a predictive model. Raw data may not be in a suitable format and may also contain biases due to differences in equipment, variations in equipment use, or variations in reporting of data. Data in the form of images, for example, needs to be converted to a matrix form for data analysis. Preprocessing also ensures that data biases do not lead to faulty predictions by detecting and correcting them. Different datasets have different preprocessing requirements and each of the steps of a preprocessing algorithm may have a plurality of parameters.

(1.2) Feature Selection

Features are independent random variables on which the outcome or the result of the analysis is dependent. In data, a lot of variables may be present. Using all of these in analysis may give misleading results for a predictive model. Feature selection is a process which performs the selection of relevant independent variables so as to enhance the accuracy of the predictive model.

(1.3) Data Integration

Data integration is the process of combining a plurality of datasets into a single dataset for data analysis. Each of the plurality of datasets may have different preprocessing needs but the combined dataset will have all the features of each of the plurality of datasets. Consequently, it will lead to high accuracy predictions and a reliable predictive model.

(1.4) Parallel Computing Network

A parallel computing network consists of a plurality of Central Processing Units (CPUs) working in parallel to provide an enhanced computational capability for the computational task allotted to the network. A parallel computing network may also allow multiple users working on a common task, thereby increasing productivity and efficiency of a workplace.

(2) Exemplary Environments to Employ Various Embodiments

Figure 1:
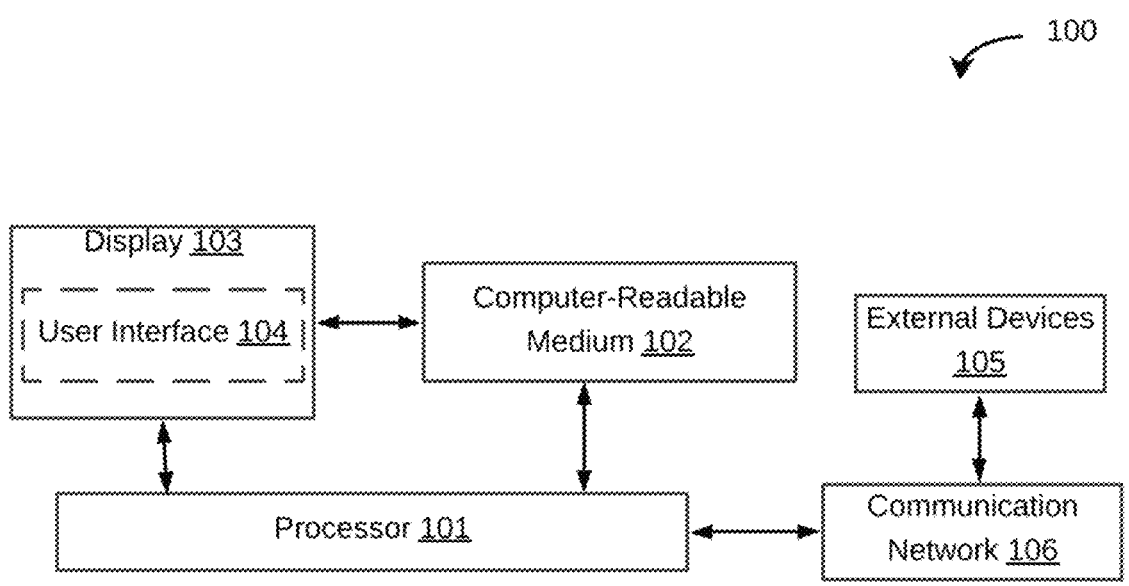
FIG. 1 is a block diagram of an exemplary system for preprocessing biomedical data, in accordance with some embodiments of the present disclosure.

Referring now to FIG. 1, an exemplary system 100 for preprocessing a biomedical data is illustrated, in accordance with some embodiments of the present disclosure. The system 100 may implement a preprocessing engine, in accordance with some embodiments of the present disclosure. In particular, the system 100 may include a preprocessing device (for example, server, desktop, laptop, notebook, netbook, tablet, smartphone, mobile phone, or any other computing device) that may implement the preprocessing engine. The preprocessing engine may preprocess the biomedical data using a machine learning (ML) algorithm.

The system 100 may include one or more processors 101, a computer-readable medium (for example, a memory) 102, and a display 103. The computer-readable storage medium 102 may store instructions that, when executed by the one or more processors 101, cause the one or more processors 101 to preprocess the biomedical data, in accordance with aspects of the present disclosure. The computer-readable storage medium 102 may also store various data that may be captured, processed, and/or required by the system 100. The system 100 may interact with a user via a user interface 104 accessible via the display 103. The system 100 may also interact with one or more external devices 105 over a communication network 106 for sending or receiving various data. The external devices 105 may include, but may not be limited to, a remote server, a digital device, or another computing system.

(3) Exemplary Systems for Various Embodiments

Figure 2A:
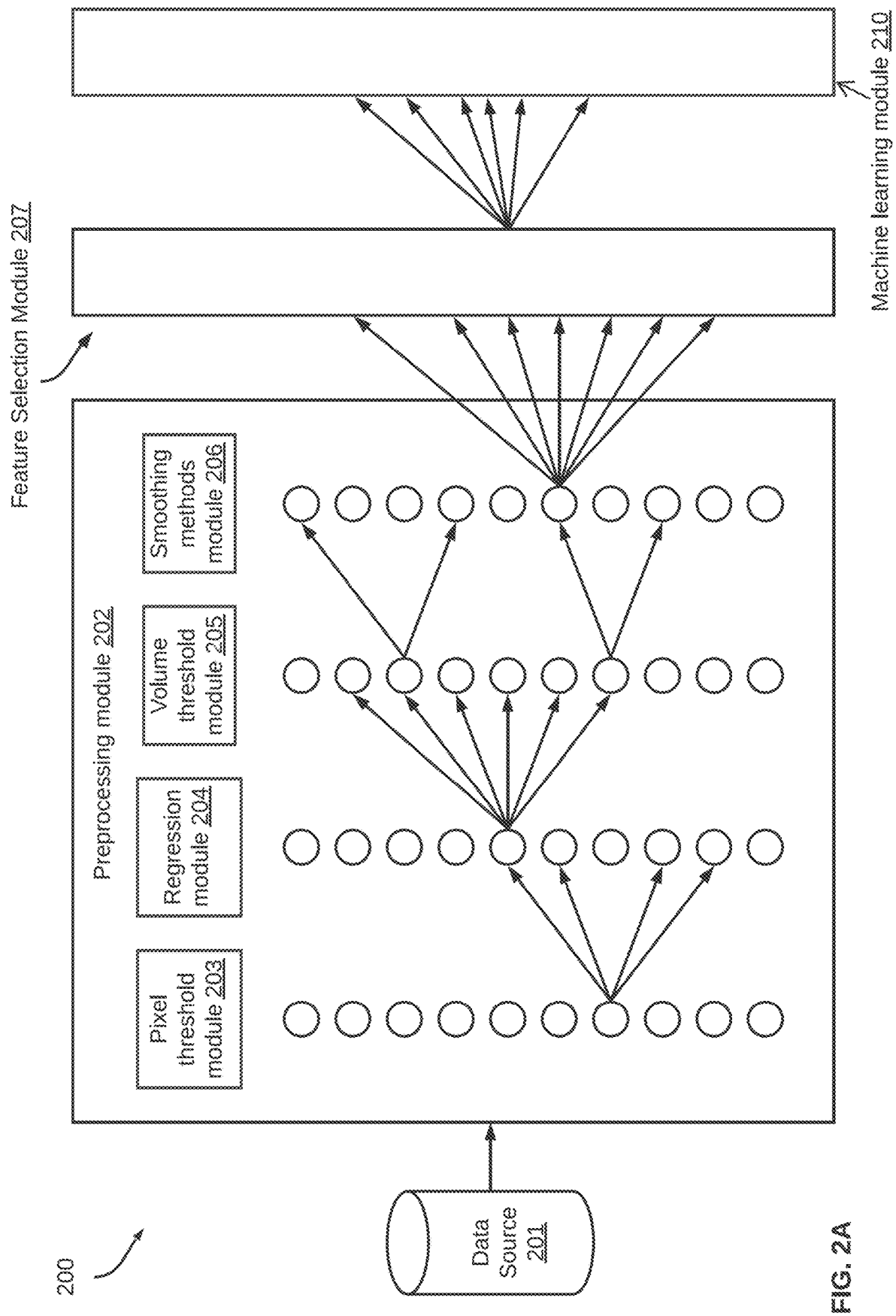
FIGS. 2A-C depict a block diagram of a machine learning (ML) framework, in accordance with some embodiments of the present disclosure.
Figure 2B:
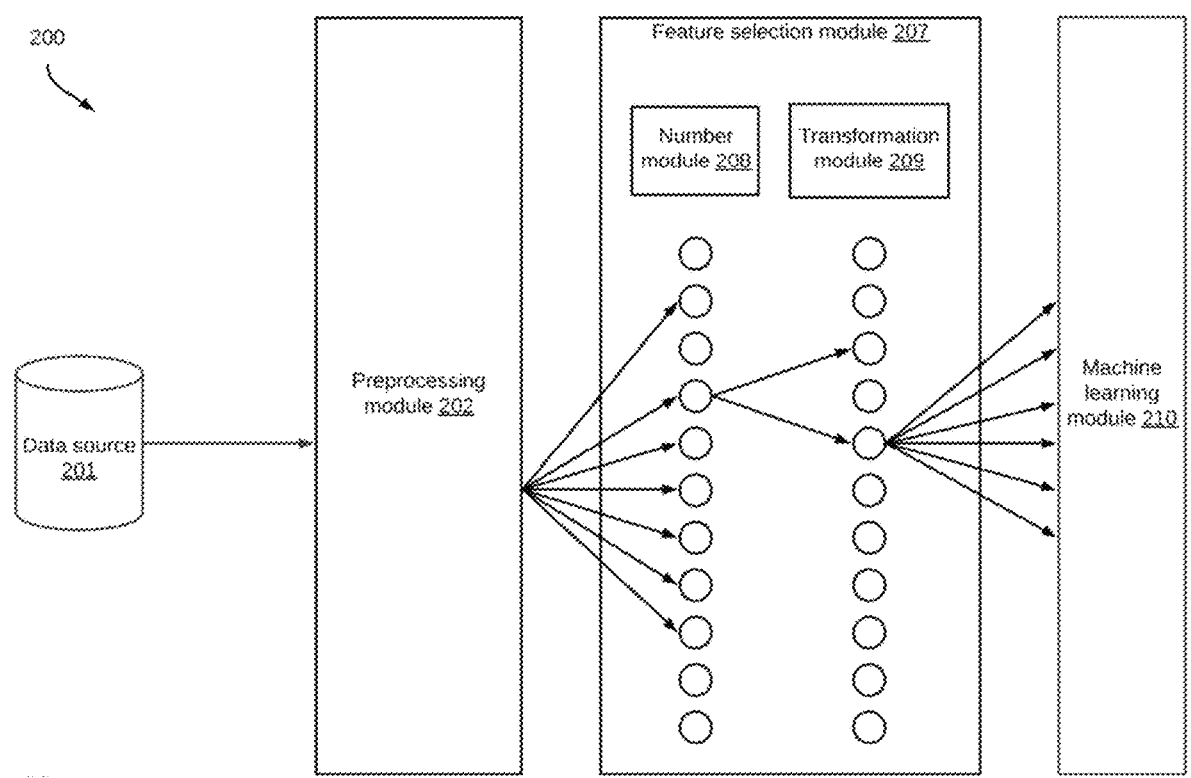
Figure 2C:
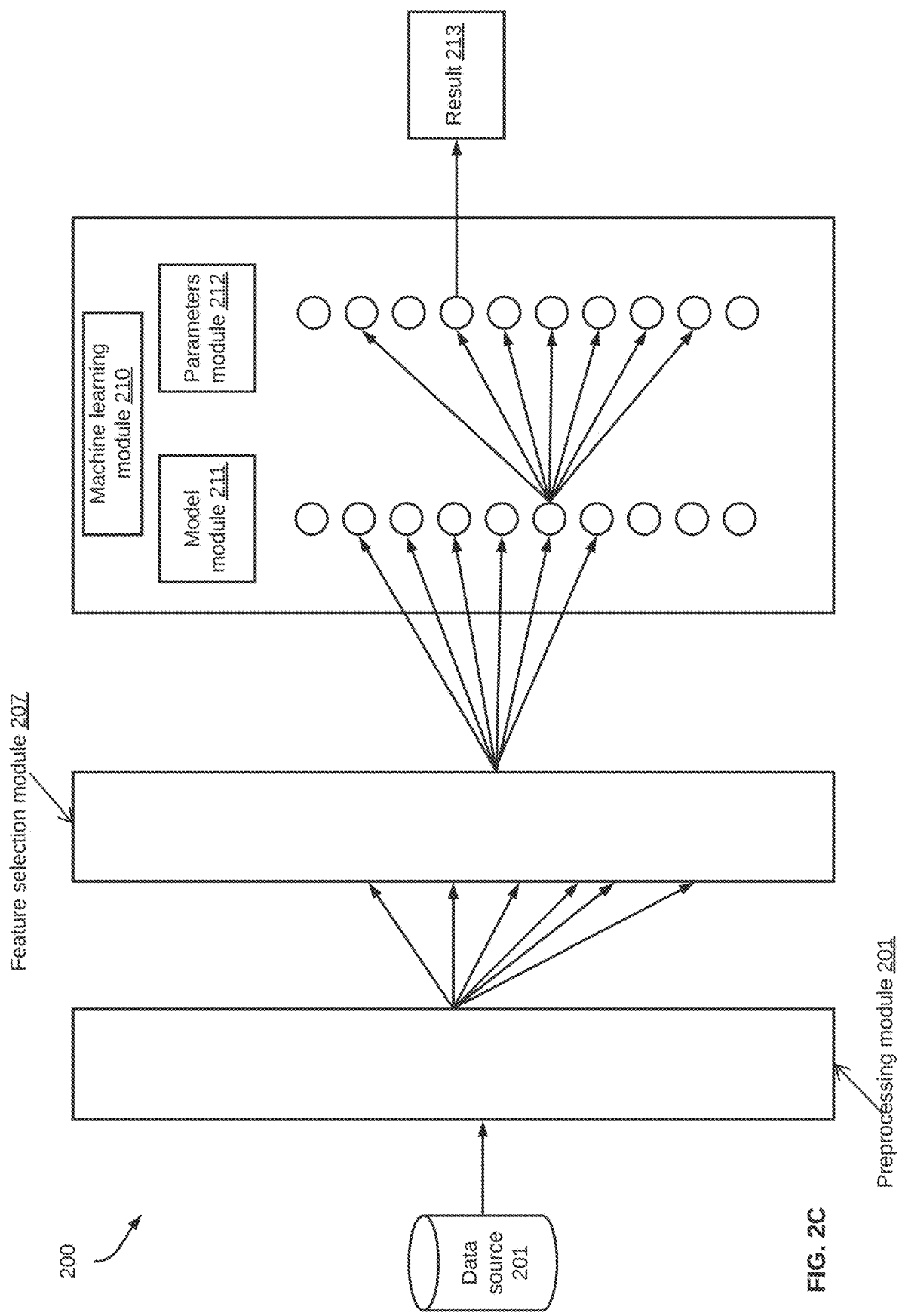

Referring now to FIGS. 2A-C, a block diagram of an ML framework 400 implemented by the system 100, is illustrated, in accordance with some embodiments of the present disclosure. The ML framework 200 includes a data source 201, a preprocessing module 202, a feature selection module 207, and an ML module 210.

The data source 201 is a system for storage of a data and provides an input data to the preprocessing module 202. Some examples include, but may not be limited to, a local storage data, a database, or a cloud storage data. There may be more than one data sources for the ML framework 200.

The preprocessing module 202 includes a pixel threshold module 203, a regression module 204, a volume threshold module 205, and a smoothing methods module 206. The preprocessing module 202 receives the input data and returns a preprocessed input data as an output.

The pixel threshold module 203 uses a pixel thresholding algorithm on the input data, wherein the input data is an image. The pixel thresholding algorithm simplifies the input data for analytical purposes. The parameters for a pixel thresholding algorithm may be an intensity of each of pixels of an image or a color of each of the pixels of the image.

The regression module 204 uses a regression algorithm to perform a preprocessing of the input data. The regression algorithm may be a linear or a non-linear regression algorithm. The preprocessing of the input data may be in the form of a transformation of the input data, a reduction in the outliers of the input data, a thresholding of the input data, a normalization of the input data, any other conventional preprocessing techniques, or any preprocessing technique yet to be discovered.

The volume threshold module 205 uses a volume thresholding algorithm on the input data, wherein the input data is a 3-dimensional (3D) image such as MRI or CT scan. The volume thresholding algorithm simplifies the input data for a volumetric analysis, wherein the volumetric analysis may be used for estimating a volume of a region (for example, a hypothalamus region of a human brain in an MRI image) from the 3D image. The parameters for a volume thresholding algorithm may include a threshold for reduction of noise in the input data and a 3-dimensional region to be analyzed.

The smoothing methods module 206 uses at least one smoothing method to simplify and generalize the input data. The smoothing methods may include, but may not be limited to, an additive smoothing algorithm, an exponential smoothing algorithm, a kernel smoother, a Laplacian smoothing algorithm, and any other data smoothing or data filtering algorithm. The use of a particular smoothing method depends on the type and distribution of the input data.

The feature selection module 207 includes a number module 208 and a transformation module 209. The feature selection module 207 receives an input data from the preprocessing module 202 and returns a set of features relevant for the predictive analysis of the predictive model.

The number module 208 generates a number of features to be used for the predictive analysis of the input data, wherein a feature is a random variable having an impact on an outcome of the predictive model. The feature selection module 207 may iterate over a range of two given numbers of features to select a suitable number of features for the predictive model.

Once the number of features is generated, the transformation module 209 then uses a transformation algorithm such as a principal component analysis (PCA), independent component analysis (ICA), or any other linear or non-linear feature transformation algorithms. The transformation algorithm converts the selected features into different functions of the selected features. A linear transformation algorithm maintains the linear relationships of a feature with other features whereas a nonlinear transformation algorithm changes the linear relationships of a feature with other features. The transformation module 209 may iterate over different transformation algorithms and their associated parameters to select a suitable transformation algorithm and a suitable set of associated parameters for the predictive model.

The ML module 210 includes a model module 211 and a parameters module 212. The ML module 210 uses an ML algorithm to perform a predictive analysis using the preprocessed data obtained from the preprocessing module 202 and the features obtained from the feature selection module 207. The predictive analysis may be, but may not be limited to, diagnosis of a disease, prediction of a probability of getting a disease, and determining an optimum treatment course for a more personalized and high precision medicine course. The ML module 210 gives a result 213 as an output. The result 213 includes the predictions of the ML framework 200 based on the input data received from the data source 201. The result 213 may be visualized using any of the standard data visualization packages such as Seaborn or Matplotlib.

The model module 211 selects a suitable predictive model, based on the data type of the input data, for performing the predictive analysis using the input data. The suitable predictive model may be a support vector machine (SVM) model, a random forest (RF) model, a neural network (NN) model, or any other ML model or a deep learning model, or a combination thereof. The model module 211 receives the preprocessed data (from the preprocessing module 202) and the features (from the feature selection module 207) as an input and generates the suitable predictive model for predictive analysis. In another embodiment, the suitable predictive model may be generated as a result of iterations performed by a second ML algorithm within the ML module 210 to determine a suitable predictive model for the input data.

The parameters module 212 iterates over a set of parameters for the predictive model generated by the model module 211 to generate a suitable value for each of the predictive model parameters. The predictive model parameters depend upon the type of the predictive model generated. For example, for an RF model, one of the predictive model parameters may be a number of decision trees, wherein each of the decision trees is a classification model, whereas for an SVM model, one of the predictive model parameters may be a type of a kernel, wherein the kernel is a set of mathematical functions for generalizing a non-linear classification problem. The parameter values may then be used to generate an ML algorithm for performing predictive analysis.

(4) Reducing Computational Time by Way of Using Parallel Computing Network

Figure 3:
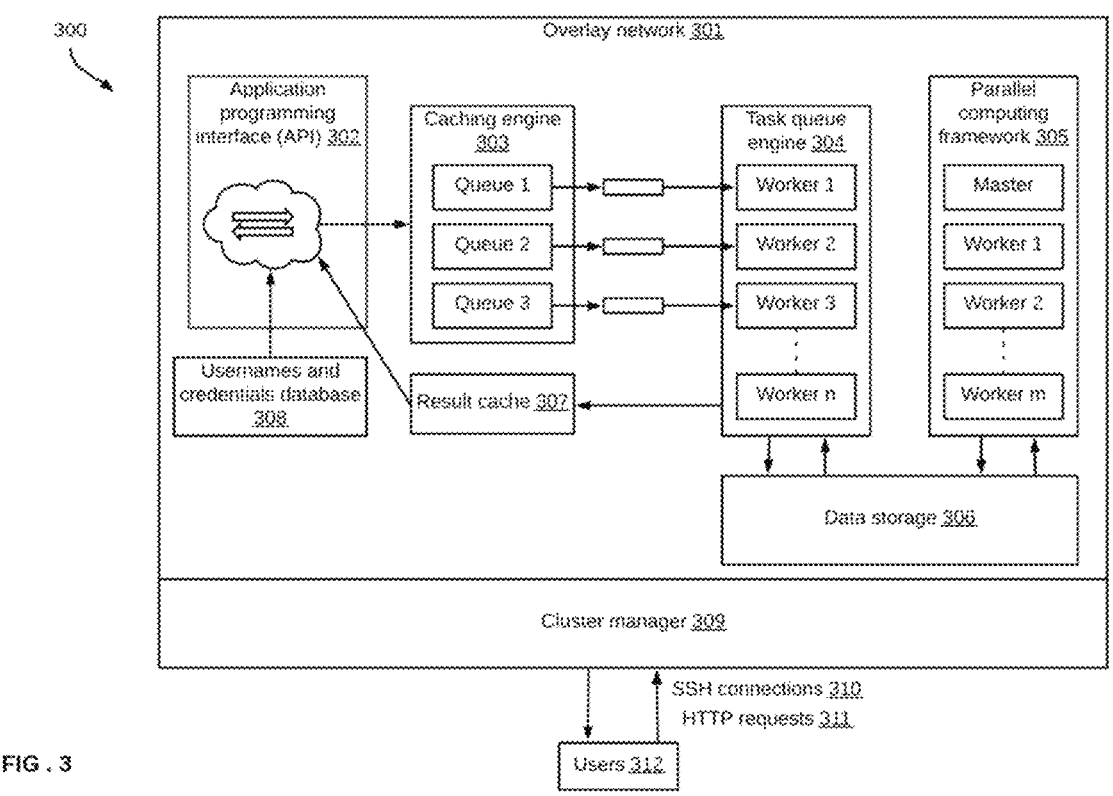
FIG. 3 is a block diagram of the ML framework of FIGS. 2A-C functioning over a parallel computing network, in accordance with some embodiments of the present disclosure.

Referring now to FIG. 3, a block diagram of the ML framework 200 of FIGS. 2A-C functioning over a parallel computing network 300, implemented by the system 100 of FIG. 1, is illustrated, in accordance with some embodiments of the present disclosure. The parallel computing network 300 includes an overlay network 301 and a cluster manager 309.

The overlay network 301 includes an application programming interface (API) 302, a caching engine 303, a task queue engine 304, a parallel computing framework 305, and a data storage 306. The overlay network 301 is a framework for enabling parallel computing for a plurality of users 312.

The API 302 is a framework to allow the parallel computing network 300, access to the data source 201. As new data entries keep adding to the data source 201, the API 302 updates continuously after a particular time interval such that the parallel computing network 300 gets access to an updated data from the data source 201. The API 302 also allows the parallel computing network 300 access to a usernames and credentials database 308, wherein the usernames and credentials of a plurality of users, such as a plurality of employees or freelancers, may be stored. A results cache 307 is received by the API 302, wherein the results cache 307 is an access layer for a result obtained by one user allowing a faster access to the result for the other users.

The caching engine 303 is a data storage in a fast access memory hardware such as a Random Access Memory (RAM). When a data is retrieved from the data source 201 for the first time, a part of its information is stored as a cache in the caching engine 303. When the data is accessed for a successive time, the cache speeds up the data access for the users 312. The caching engine 303 may be based on Redis or any other data structure capable of running as a cache framework.

The task queue engine 304 is a data structure containing a list of tasks to be performed in the background. The tasks may be, retrieval of an updated data from the data source 201 or retrieval of results from the data storage 306. If the data from the data source 201 has been previously retrieved, the caching engine 303 allows a faster access to the data source 201 for the task queue engine 304. The task queue engine 504 may be based on Celery or any other task queue framework.

The parallel computing framework 305 is a framework to allow a plurality of users 312 to work together on a common input data. The parallel computing framework 305 also allows a containerized deployment of algorithms for a faster execution of the preprocessing, the feature selection, the predictive model, and an integration of multiple data types, wherein the integration of multiple data types is combining a plurality of datasets into a common dataset to obtain an increased set of features and a higher accuracy. The containerized deployment includes a plurality of containers or modules, each of which is deployed with at least one algorithm to execute. Each container may package an application together with libraries and other dependencies to provide isolated environments for running the application. The parallel computing framework 305 may be based on Apache Spark or any other parallel computing platform. The data and results obtained by the parallel computing framework 305 are stored in the data storage 306.

The data storage 306 is primarily accessible by the users 312. The data storage 306 is a relatively local data storage when compared to the data source 201. It may include the data received from the parallel computing framework 305 and the data received from the data source 201 via the task queue engine 304.

The cluster manager 309 receives a user query from at least one user 312 via a Secure Shell (SSH) connection 310 or a Hyper Text Transfer Protocol (HTTP) request 311 and sends the user query to the overlay network 301. The cluster manager 309 also receives an output from the overlay network 301 and sends the output to each of the users 312 via the SSH connection 310 or the HTTP request 311.

(5) Iterative Preprocessing Input Data

Figure 4:
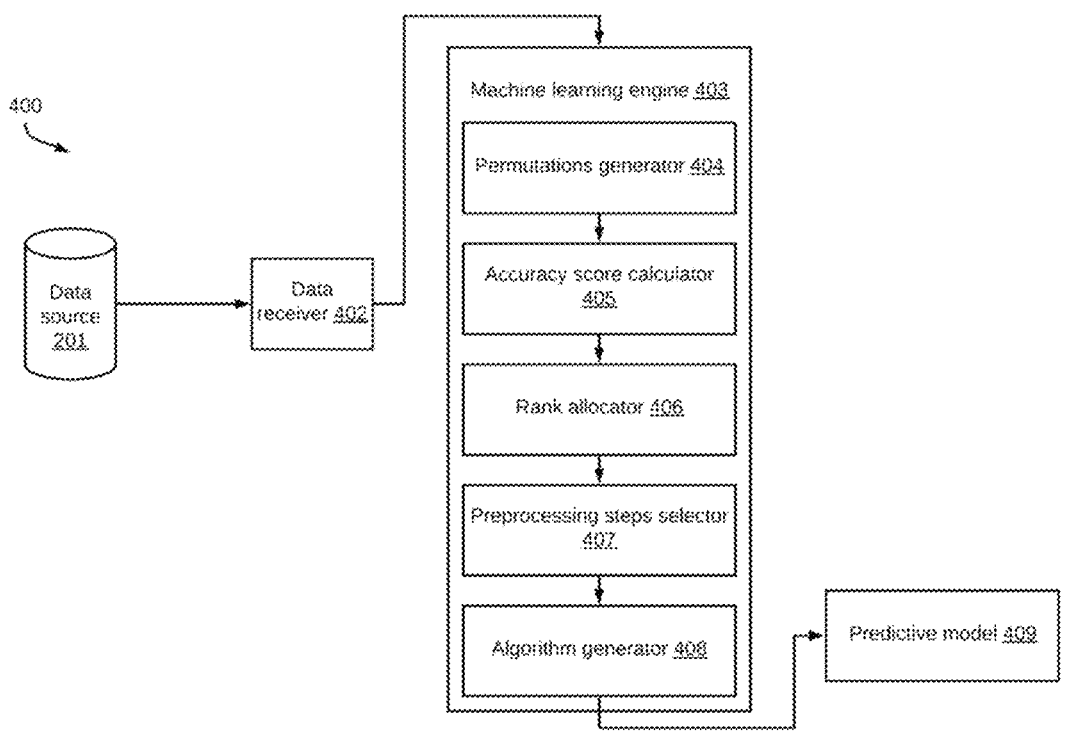
FIG. 4 is a block diagram of a preprocessing engine, in accordance with some embodiments of the present disclosure.

Referring now to FIG. 4, a block diagram of a preprocessing engine 400, implemented by the system 100 of FIG. 1, is illustrated, in accordance with some embodiments of the present disclosure. The preprocessing engine 400 includes a data source 201, a data receiver 402, an ML engine 403, and a predictive model 409.

The data source 201 is a system for storage of a data and provides an input data to the ML engine 403. Some examples include, but may not be limited to, a local storage data, a database, or a cloud storage data. The data receiver 402 receives the input data and identifies a data type of the input data. The input data is then transferred by the data receiver 402 to the ML engine 403.

The ML engine 403 further includes a preprocessing steps predictor 404, an accuracy score calculator 405, a rank allocator 406, a preprocessing steps selector 407, and an algorithm generator 408. The ML engine 403 contains a plurality of ML algorithms for different data types. The data receiver 402 identifies the data type of the input data and sends the information to the ML engine 403. One or more than one suitable ML algorithms can then be applied on various preprocessing parameters, based on the data type of the input data, to generate a specific and suitable preprocessing algorithm for the input data. The data types may include, but may not be limited to, Magnetic Resonance Imaging (MRI), functional Magnetic Resonance Imaging (f MRI) data, an Electroencephalogram (EEG) data, an Electrocardiogram (EKG/ECG) data, a genetics data, a proteomics data, data from wearable devices, an Electronic Health Record (EHR) data, and Electronic Medical Record (EMR) data, Chemistry (SMILES, InCHI, SDF), Images (PNG, JPEG) and other healthcare related data options. The preprocessing parameters may include, but may not be limited to, a pixel threshold, a linear/nonlinear regression, a volume threshold, and a smoothing method.

The preprocessing steps predictor 404 uses the ML algorithm to identify the data type and generate various permutations of the preprocessing parameters. These permutations are then applied on a test data (a subset of the input data) to check for their respective prediction accuracy scores by the accuracy score calculator 405. The accuracy score may be classification accuracy, logarithmic loss, confusion matrix, area under curve, F1 score, mean absolute error, mean squared error, or any other performance evaluation metric.

Classification accuracy is the ratio of number of correct predictions to the total number of predictions made. It can be represented as per equation (1) below:

Accuracy=Correct/Total, (1)

where Correct=number of correct predictions made
Total=total number of predictions made
Logarithmic loss penalizes false classifications and can be represented as per equation (2) below:

$$\text{Log loss} = \frac{-1}{N}\left(\sum_{i=1}^{N}\sum_{j=1}^{M} y_{ij} * \log(p_{ij})\right) \quad (2)$$

where,
N samples belong to M classes
y_ij, indicates whether sample i belongs to class j or not
p_ij, indicates the probability of sample i belonging to class j Confusion matrix metric gives a matrix as an output describing the accuracy of each of the predictions made by the model. It sorts out each prediction as True Positives (TP), where the prediction as well as observation both were true, True Negatives (TN), where the prediction as well as observation both were false, False Positives (FP) where the prediction was true but the observation was false, False Negatives (FN), where the prediction was false but the observation was true. Accuracy for a confusion matrix can be represented as per equation (3):

Accuracy=(TP+TN)/(N) (3)

Where, N=total number of samples
Area under curve (AUC) uses a curve called receiver operating characteristic (ROC) curve to evaluate the performance of a model. ROC curve is a plot of specificity vs sensitivity of a model where:

Specificity=(FP)/(FP+TN) (4)

and Sensitivity=(TP)/(FN+TP) (5)

Area under the ROC curve is calculated and a model with high AUC is considered better performing.
F1 score is a harmonic mean of precision and recall, where:

Precision=(TP)/(TP+FP) (6)

Recall=(TP)/(TP+FN) (7)

F1score=2*(1/precision+1/recall)$^{-1}$ (8)

Mean absolute error is the average of the difference between the observations and the predictions.

$$\text{Mean absolute error} = \frac{1}{N}\sum_{j=1}^{N}|y_j - \hat{y}_j| \quad (9)$$

Where y_j is an observed value and ŷ_j is a predicted value.
Mean squared error is the average of the square of the difference between the original values and the predicted values.

$$\text{Mean squared error} = \frac{1}{N}\sum_{j=1}^{N}(y_j - \hat{y}_j)^2 \quad (10)$$

The rank allocator 406 then arranges the various permutations in the decreasing order of their respective accuracy scores and assigns a rank in that order to each permutation or a predetermined number of permutations. The preprocessing steps selector 407 selects the top-ranked or a specified number of the permutations of preprocessing parameters. If more than one permutation is selected, the selected permutations may be displayed as options to the user. The user may then select a suitable option for a more customized preprocessing based on the research requirements. The algorithm generator 408 then uses the top-ranked or user selected permutation of preprocessing parameters to generate an optimized preprocessing algorithm. The predictive model 409 then performs data analysis using the optimized preprocessing algorithm.

Figure 5:
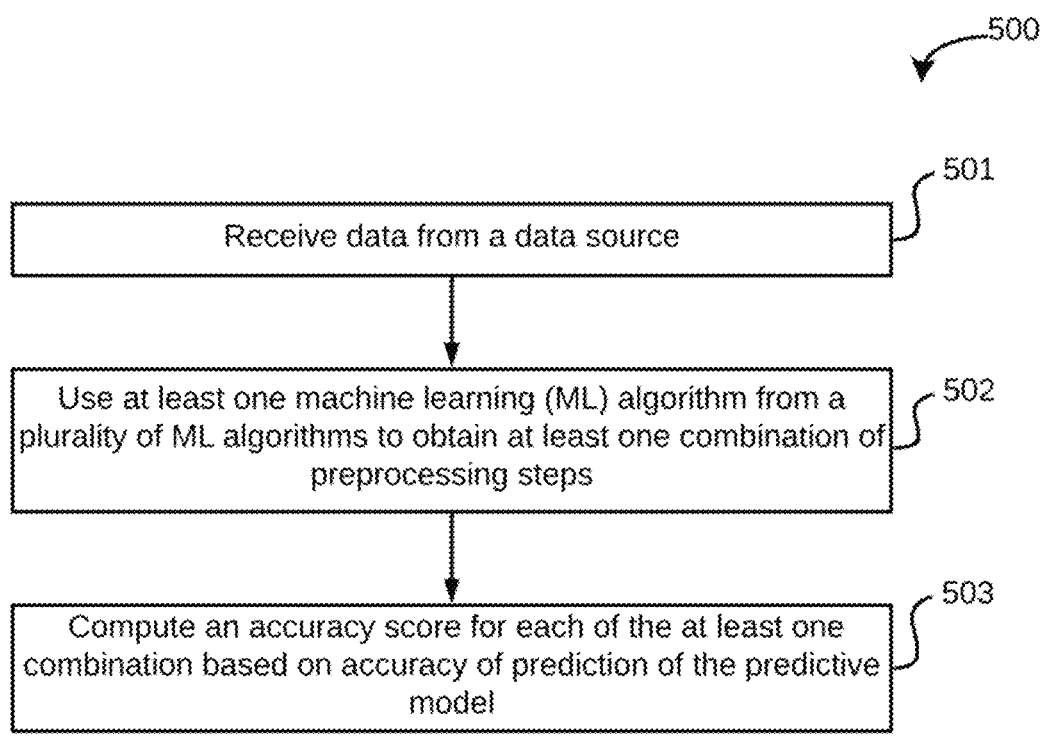
FIG. 5 is a flow diagram of an exemplary process for preprocessing biomedical data, in accordance with some embodiments of the present disclosure.

Referring now to FIG. 5, a flow diagram of an exemplary process 500 for preprocessing biomedical data, is illustrated, in accordance with some embodiments of the present disclosure. At step 501, the input data is received by the data receiver 402 from the data source 201. The data source 201 may be a part of the computer-readable medium 102 or one or more than one external device 105. The input data may be one or more than one large dataset. At step 502, at least one ML algorithm from a plurality of ML algorithms is applied, by the ML engine 403, on the preprocessing parameters to obtain at least one combination of preprocessing steps. The plurality of ML algorithms may include ML algorithms particularly created for biomedical data types, such as Magnetic Resonance Imaging (MRI), functional Magnetic Resonance Imaging (fMRI) data, an Electroencephalogram (EEG) data, an Electrocardiogram (EKG/ECG) data, a genetics data, a proteomics data, data from wearable devices, an Electronic Health Record (EH R) data, and Electronic Medical Record (EMR) data, Chemistry (SMILES, InCHI, SDF), Images (PNG, JPEG) and other healthcare related data options. At step 503, an accuracy score for each of the at least one combination of preprocessing steps is computed by the accuracy score calculator 405. The accuracy score may then be used as a basis for selecting a suitable combination of preprocessing parameters, leading to a suitable permutation of preprocessing steps.

Figure 6:
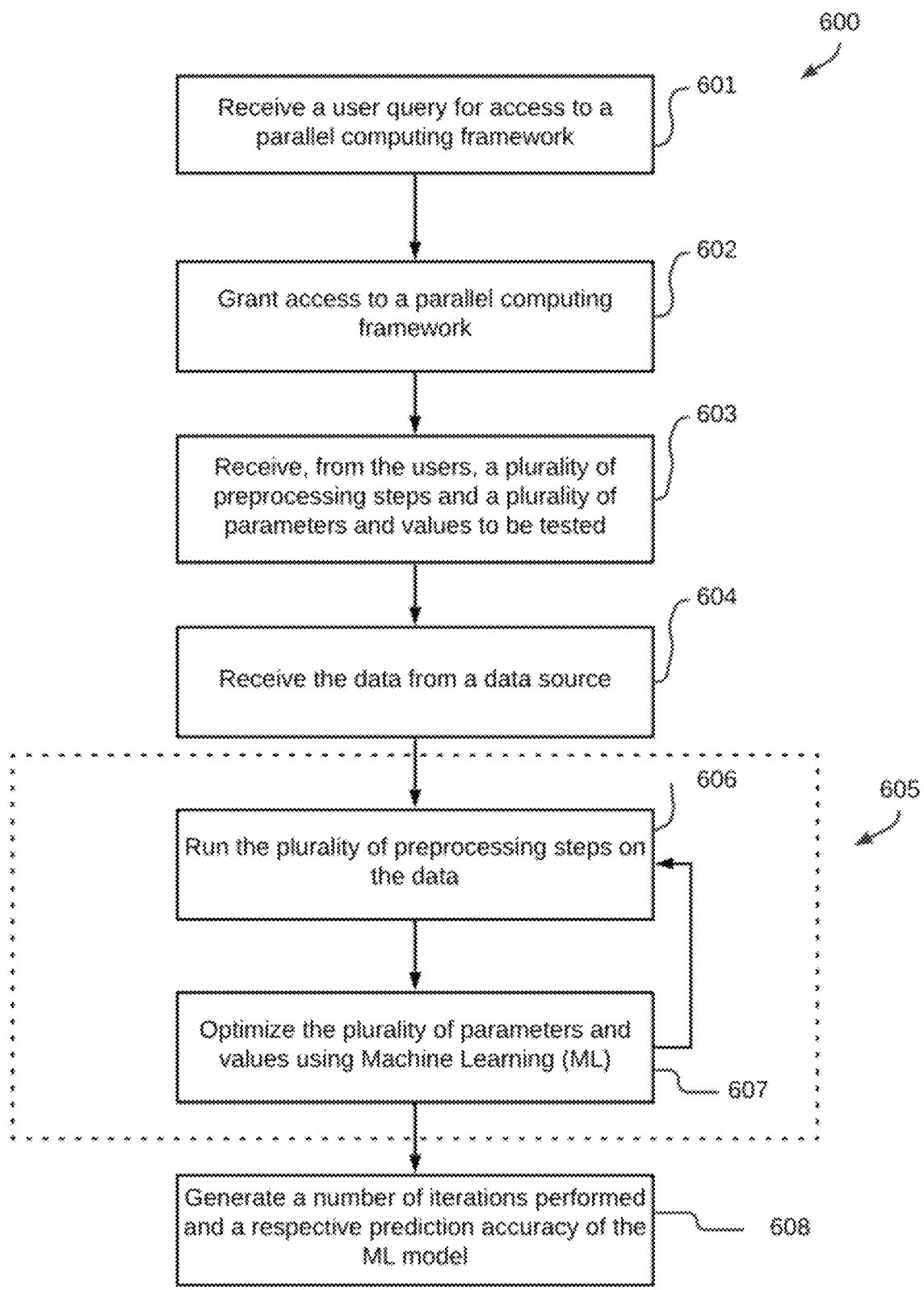
FIG. 6 is a flow diagram of an exemplary process of preprocessing biomedical data using the parallel computing network of FIG. 3, in accordance with some embodiments of the present disclosure.

Referring now to FIG. 6, a flow diagram of an exemplary process 600 of preprocessing biomedical data using the parallel computing network 300 of FIG. 3, is illustrated, in accordance with some embodiments of the present disclosure. An ML process 605 is also depicted within the process 600. As illustrated in the flow diagram, at step 601 of the process 600, the parallel computing network 300 may receive a user query from the users 312 for access to the parallel computing framework 305. Consequently, at step 602, the parallel computing network 300 may then grant access to the parallel computing framework 305.

At step 603, the parallel computing framework 305 may receive, from the users 312, a plurality of preprocessing steps and the plurality of parameters and values to be tested for each of the preprocessing steps. The users 312 may define a sequence of the preprocessing steps. At step 604, once the sequence of the preprocessing steps is defined, the parallel computing framework 305 may receive the data from the data source 201 via the API 302.

The ML process 605 for preprocessing the input data is depicted in the flow diagram. Within the ML process 605, at step 606, the ML engine 403, implemented by the parallel computing framework 305, may run the plurality of preprocessing steps on the data. At step 607, the ML engine 403, implemented by the parallel computing framework 305, may optimize the plurality of parameters and values for each of the preprocessing steps of step 606 using an ML algorithm. The ML process 605 may be an iterative process wherein the plurality of parameters and values may be used in the preprocessing steps of step 606 and tested, on a test sample of the input data, for the associated prediction accuracy by using the accuracy score calculator 405.

At step 608, the parallel computing framework 305 may generate a number of iterations performed, using the plurality of parameters and values of each of the preprocessing steps, and a respective prediction accuracy of each of the iterations.

(6) Data Integration and Feature Selection

Figure 7:
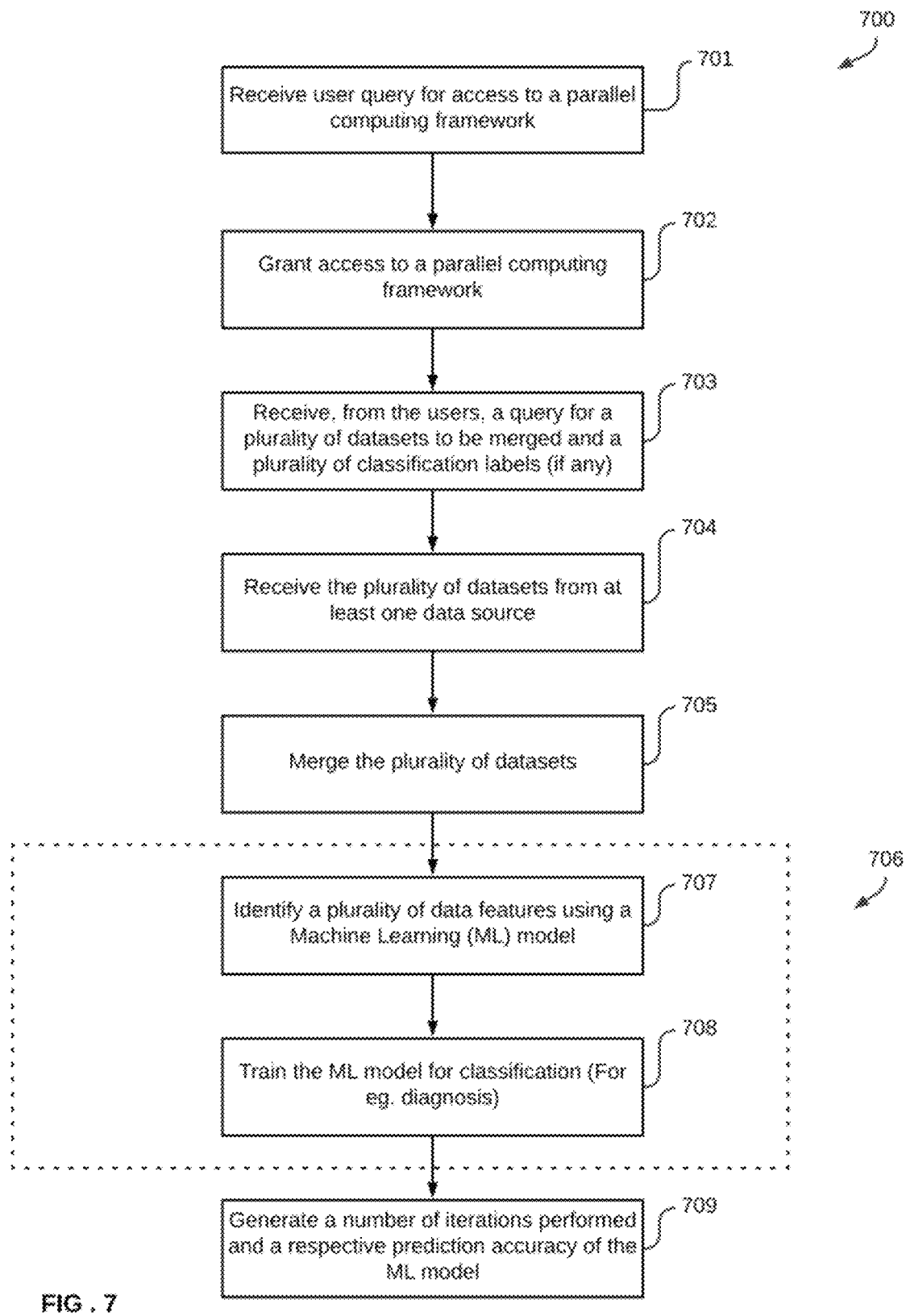
FIG. 7 is a flow diagram of an exemplary process of merging a plurality of datasets and selecting relevant features from the combined dataset using the parallel computing network of FIG. 3, in accordance with some embodiments of the present disclosure.

Referring now to FIG. 7, a flow diagram of an exemplary process 700 of merging a plurality of datasets and selecting relevant features from the combined dataset using the parallel computing network 300 of FIG. 3, is illustrated, in accordance with some embodiments of the present disclosure. A feature selection process 706 is also depicted within the process 700. As illustrated in the flow diagram, at step 701, the parallel computing network 300 may receive a user query from the users 312 for access to the parallel computing framework 305. Consequently, at step 702, the parallel computing network 300 may then grant access to the parallel computing framework 305.

At step 703, the parallel computing framework 305 may receive, from the users 312, a query for a plurality of datasets to be merged and a plurality of classification labels (if any). The plurality of datasets may have different data sources. At step 704, the parallel computing network 305 may receive the plurality of datasets from at least one data source. At step 705, the parallel computing network 305 may merge the plurality of datasets to give a combined dataset.

The feature selection process 706 for selecting the plurality of relevant features from the input data is depicted in the flow diagram. Within the feature selection process 706, at step 707, the parallel computing network 305 may identify a plurality of data features using a ML model. The ML model allows prediction of relevant data features, automating the feature selection process 706. At step 708, the parallel computing network 305 may train the ML model for classification problem such as diagnosis using the features obtained in step 707.

At step 709, the parallel computing network 305 may generate a number of iterations performed, using the features selected by the ML models of step 707, and a respective prediction accuracy of each of the ML models.

Figure 8:
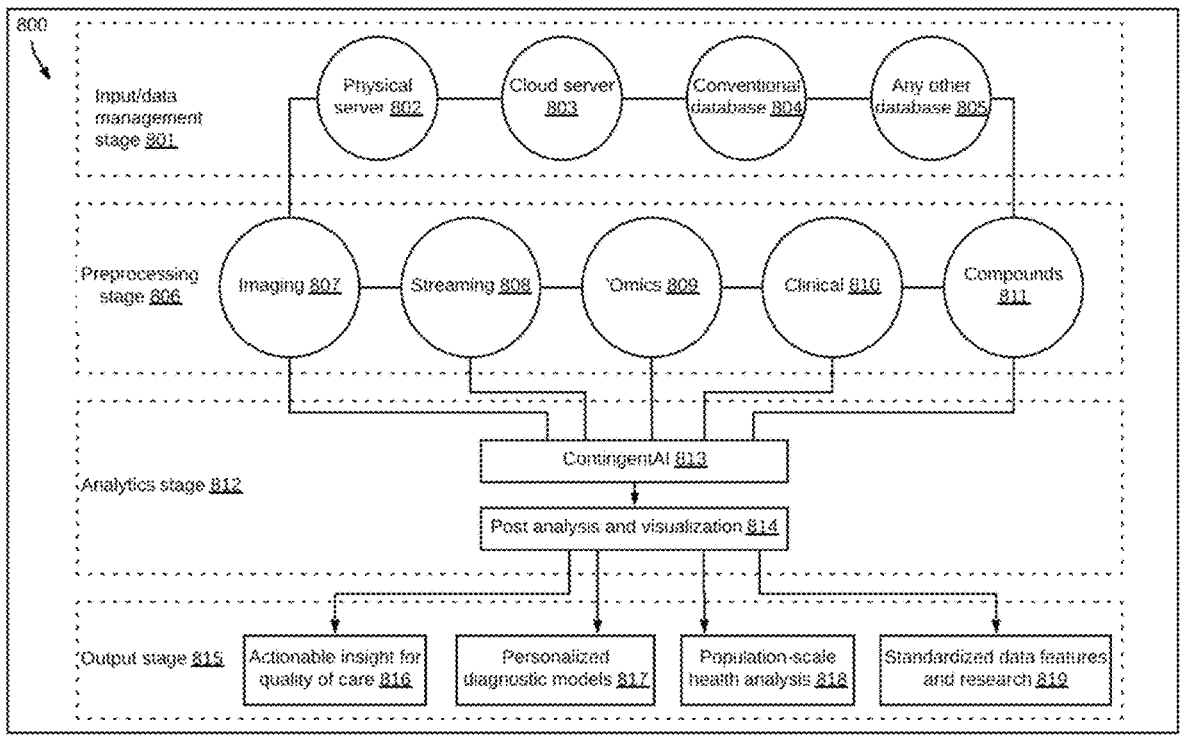
FIG. 8 is a block diagram depicting the examples of input sources and operations performed by the parallel computing network of FIG. 3, in accordance with some embodiments of the present disclosure.

Referring now to FIG. 8, a block diagram of the examples of input sources and operations 800 performed by the parallel computing network 300 of FIG. 3, is illustrated, in accordance with some embodiments of the present disclosure. The examples of input sources and operations 800 of the parallel computing network 300 include the examples of an input/data management stage 801, a preprocessing stage 806, an analytics stage 812, and an output stage 815.

The examples of the input/data management stage 801 include a physical server 802, a cloud server 803, a conventional database 804, and an any other database 805. The examples of the preprocessing stage 806 include an imaging 807, a streaming 808, an omics 809, a clinical 810, and compounds 811.

The analytics stage 812 is implemented by a ContingentAI 813, wherein the ContingentAI 813 is an artificial intelligence (AI)/ML based framework for big data analytics of biomedical data. The post analysis and visualization 814 of the results are sent as output to the output stage 815.

The examples of the output stage 815 include an actionable insight for quality of care 816, personalized diagnostic models 817, a population-scale health analysis 818, and a standardized data features and research 819.

(7) Variations on the Above Embodiments

It may be useful to arrange for the permutation generator 404 to generate ordered permutations based on previous rankings of configurations from the rank allocator 406.

It may be useful for the machine learning engine 403 to consider permutations in ranked order and to halt consideration when the accuracy score calculator 405 exceeds a specified threshold.

It may be useful to add pre-classified challenge data to the data source 201 in order to avoid certain sampling biases which may be present in the input data.

It may be useful to have the rank allocator 406 to weight accuracy scores 405 based on the accuracy of similar configurations against benchmarked data samples.

It may be useful for the machine learning algorithm 403 to evaluate the dependence or independence of choices in preprocessing 201 or feature selection 202. This evaluation may be used to reduce the total number of permutations to be examined.

It may be useful for the machine learning algorithm 403 to be seeded with rules or meta models for the selection of models 211 or hyperparameters 212 for the machine learning module 210.

It may be useful for the post analysis and visualization component 814 to present a plurality of results 213 as generated by different combinations of pre-processing steps and selections of features.

It may be useful for the post analysis and visualization component 814 to indicate areas of agreement or disagreement across models 210 generated by different combinations of pre-processing steps, feature selections, and model/hyperparameter settings.

It may be useful to arrange for the preprocessing engine 400 to accept pre-processing steps as defined by a particular programming language. The particular programming language can typically be a higher level programming language directed towards efficient coding of automated pre-processing tasks. It may be useful for the particular programming language to point out certain pre-processing tasks to be performed by the preprocessing engine.

(8) Combining Preprocessing Steps and Integration of Heterogeneous Datasets

Biological samples by their nature are inherently variable and so when these are analysed it is generally necessary to apply data pre-processing procedures to compensate for these differences which may stem from sample size differences, unavoidable baseline shifts, missing data points, containing errors and outliers or lacking certain attributes or values.

There are many different algorithms available to choose from to establish a sensible pre-processing procedure. The procedure may include a data mining technique or algorithm that involves transforming raw data into a more processed format. They also may include methods to remove non-biological signal (bias) from the data that is introduced due to surveyor, equipment, or some other aspect of the experimental design. Below discussed are exemplary methods related to optimization of pre-processing data, and integration of these pre-processing methods with the machine learning process.

In some embodiments, the machine learning process comprises a preprocessing process, a training process, and a prediction process. The data processing process may extract training data from a database or a user, apply one or more transformations to standardize the training data, and pass the standardized training data to the training process. The training process may construct an assessment model based on the standardized training data. The prediction process may generate a predicted classification of the subject.

In some embodiments, the training process utilizes a machine learning algorithm to construct and train the assessment model.

In some embodiments, the prediction process generates the predicted classification of the subject by fitting new data to the assessment model, the new data being standardized by the preprocessing process. The prediction process may check whether the fitting of the new data generates a prediction of one or more specific disorders within a confidence interval exceeding a threshold value.

In some embodiments, the prediction process comprises a question recommendation process. The question recommendation process may identify, select, or recommend the most predictive next question to be asked with the subject, based on the plurality of answers to the plurality of asked questions, so as to reduce a length of assessment. The question recommendation process may select one or more candidate questions for recommendation as the next question to be presented to the subject. The question recommendation process may evaluate an expected feature importance of each one of the candidate questions. The question recommendation process may select one or more most predictive next question from the candidate questions, based on the expected feature importance of each one of the candidate questions. The expected feature importance of each one of the candidate questions may be determined with an expected feature importance determination algorithm.

The algorithm combines, feedback, activities, or interactions provided to select suitable combination of preprocessing steps, which can be ultimately customized by the user depending on need, origin of data, and other input. It may be used on human models or predictive algorithms.

The preprocessing module can be configured to apply one or more transformations to the extracted training data to clean and normalize the data, for example. The preprocessing module can be configured to discard features which contain spurious metadata or contain very few observations.

The preprocessing module can be further configured to standardize the encoding of feature values. Different datasets may often have the same feature value encoded in different ways, depending on the source of the dataset.

The preprocessing module can be configured to recognize the encoding variants for the same feature value, and standardize the datasets to have a uniform encoding for a given feature value. The preprocessing module can thus reduce irregularities in the input data for the training and prediction modules, thereby improving the robustness of the training and prediction modules.

In addition to standardizing data, the preprocessing module can also be configured to re-encode certain feature values into a different data representation. In some instances, the original data representation of the feature values in a dataset may not be ideal for the construction of an assessment model.

The preprocessing module can be further configured to impute any missing data values, such that downstream modules can correctly process the data. For example, if a training dataset provided to the training module comprises data missing an answer to one of the questions, the preprocessing module can provide the missing value, so that the dataset can be processed correctly by the training module. Similarly, if a new dataset provided to the prediction module is missing one or more feature values (e.g., the dataset being queried comprises only the answer to the first question in a series of questions to be asked), the preprocessing module can provide the missing values, so as to enable correct processing of the dataset by the prediction module.

The term 'plurality of datasets' can have several meanings. Datasets that have the same format, but are gathered using different machines of the same type can be considered different types of data.

Small differences in testing environments can also lead to different patterns in datasets which will be recognized by an ML algorithm as such, although undesired. Datasets that are gathered by different types of machines are also heterogeneous. The preprocessing module includes bias correction steps and parameters to homogenize data gathered by the same type of machine.

The preprocessing module could include different bias correction techniques to be varied, so that the type of bias correction could be included in the variation of preprocessing steps. Thus, the effect of each bias correction technique and each variation of parameters associated with the technique could be measured by calculating the accuracy of each predictive model quantity against the associated empirical quantities.

It is also important to integrate different types of data (i.e. data gathered by different types of machines) into the ML predictive model. It has been shown that using different types of data together in a single predictive model can lead to more accurate predictions. This can be achieved by allowing the preprocessing module to consider multiple heterogeneous datasets at the same time with the same algorithm.

This way, the preprocessing module can include variations of feature selection steps for each type of data. For example, a permutation of two types of feature selection on a single type of data would only lead to four types of permutations (neither, one, the other, or both). However, if two types of data are considered simultaneously and each type of data allows for two types of feature selection, the total number of permutation types would rise to sixteen.

The effects of each feature selection permutation on the combined dataset could also be measured by calculating the accuracy of each predictive model quantity against the associated empirical quantities. Thus, the machine learning preprocessing algorithm includes parameters for bias correction in order to homogenize datasets of the same format and feature selection parameters to simultaneously consider and integrate datasets of different formats for higher predictive accuracy.

Figure 10:
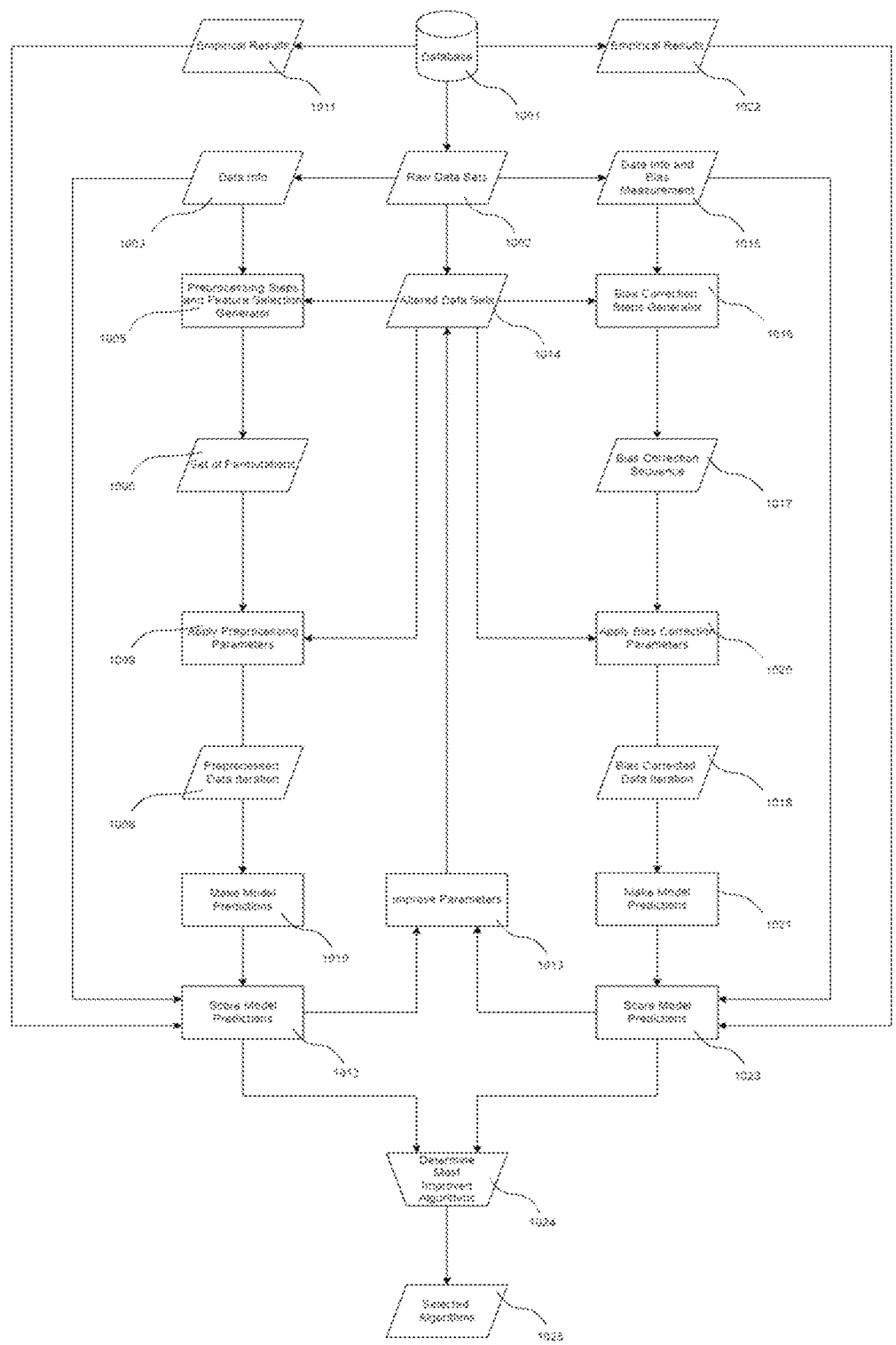
FIG. 10 is a flow diagram of an exemplary process of preprocessing parameter optimization included in the ML predictive model creation process.

FIG. 10 is related to a flow diagram of an exemplary process of preprocessing parameter optimization included in the ML predictive model creation process.

Referring to FIG. 10, the database 1001 first gathers the raw data sets 1002 and sends administrative information about the data 1003 to the permutation generator 1005. The information about the data includes the type of data, the machine used to gather the data, the file format used to store the data, and any other relevant information that could be used by the permutation generator 1005.

The type of data could be anything relevant to the predictive model, but some examples are Magnetic Resonance Imaging (MRI), functional Magnetic Resonance Imaging (fMRI) data, an Electroencephalogram (EEG) data, an Electrocardiogram (EKG/ECG) data, a genetics data, a proteomics data, data from wearable devices, an Electronic Health Record (EHR) data, and Electronic Medical Record (EMR) data, Chemical Structures (SMILES, InCHI, SDF), Images (PNG, JPEG), including from pathology or other applications of microscopy, and other healthcare and medical research related data options.

The permutation generator 1005 then generates a number of preprocessing and feature selection steps, varying in both step selection and order of steps, and accompanying preprocessing parameters that are suitable for the type of data received. The set of generated permutations 1006 are sent to the algorithm generator 1007. The algorithm generator 1007 takes the permutation steps and turns each permutation into an algorithm that can be applied to the data. The full set of generated algorithms 1007 are sent to module 1009 to be applied to the data.

The raw data 1002 is sent to an editable placeholder module 1014, where the raw data can be altered without compromising the raw data, so that it can be reused after alteration if necessary.

The module 1009 takes the data from the placeholder module 1014 and applies the algorithms from module 1008. The algorithm application process results in a set of model predictions 1010 which can then be sent to module 1012. Module 1012 takes the set of model predictions 1010 as well as the administrative information about the data 1003 and finally the associated empirical results 1011. Module 1012 uses scoring techniques such as cross validation to compare the predicted quantities to the empirical quantities and calculates a number of accuracy measurements, including but not limited to classification accuracy, logarithmic loss, confusion matrix, area under curve, F1 score, mean absolute error, or mean squared error.

The accuracy scores are sent to module 1013, which aims to find the parameters that give the highest accuracy scores. The techniques used by this module include random search and grid search hyperparameter optimization. The process repeats by looping back to the data placeholder module 1014 and applying different preprocessing and feature selection algorithms, thereby generating different accuracy scores for each set of permutations.

At the same time as the preprocessing and feature selection permutation loop, other administrative information about the data 1015 and the placeholder data 1014 is sent to the bias correction steps generator 1016, where the focus is on debiasing the data.

Biases in datasets can include a selection bias, a reporting bias, a recall bias, an exclusion bias, an information bias, or a statistical bias. Most importantly, in biological data collection the most common bias is site bias, where even if the same experiment is conducted but across different locations, the resulting data will be skewed for various reasons.

Similarly, these non-biological signals can be attributed to confounding variations in personnel, date of data collection, well location etc. In order to mitigate these biases, the module 1015 can also use various algorithmic methods to quantify each type of relevant bias in each data set. For example, if the dataset came from a cohort study, the selection bias can be quantified by calculating the relative odds ratio and its standard error.

When collecting data for the study of various biological signals, it is possible for the signal to be corrupted in systematic ways due to the design of the experiments. In addition to the types of biases listed above, one common bias that the pre-processing steps aim to diminish can be referred to as site bias. If the same experiment is conducted across different locations, it is expected for the resulting data to be skewed in location A vs location B. Similarly, these non-biological signals can be attributed to confounding variations in personnel, date of data collection etc.

Bias is measured in several ways but strategies for accurate confounder analysis are not in abundance. Standard linear methods suffer from outlier sensitivity, are blind to complex structure in data, and cannot disambiguate hierarchically nested confounders; matching and stratification strategies suffer on high-dimensional data due to combinatorial scaling of unmatched dimensions, and matching is impossible for a lower-level confounder in a nested hierarchy; and Bayesian models suffer from poor performance in high dimensions.

Therefore, some embodiments may reduce non-biological signal and maximize biological signal concurrently through customized bias detection method as seen in module 1015 paired with iterative trials of varying batch correction algorithms as seen in module 1016 to 1020.

In low dimensional data, each variable can be plotted and visually attributed to each potential confounding variable.

In high dimensional data, even visual detection of bias is difficult and requires preprocessing the data using principal component analysis and subsequently visualizing whether data aggregate according to confounding variables in top-level components. This same strategy can be formed via any dimension reduction strategy (UMAP, t-SNE, etc.)

The bias correction steps generator takes the placeholder data 1014 and the data and bias info 1015 and generates a number of steps to correct the quantified biases to a suitable degree. For example, if the bias is a selection bias, a suitable bias correction method among a number of suitable methods could be an inverse probability weighting technique. If the data also possesses another quantified bias, like a statistical bias, a suitable bias correction method among a number of suitable methods could be a quantile mapping technique. For every quantified bias in a data set, the bias correction steps generator generates a number of permutations of bias correction steps, varying in both the bias correction technique and the order in which each step is applied, and accompanying bias correction parameters.

To give an example, if the model is more accurate at predicting the day of the week that sample is collected in contrast to a biological signal, it is considered for that dataset to be biased to towards non-biological signal.

Figure 15:
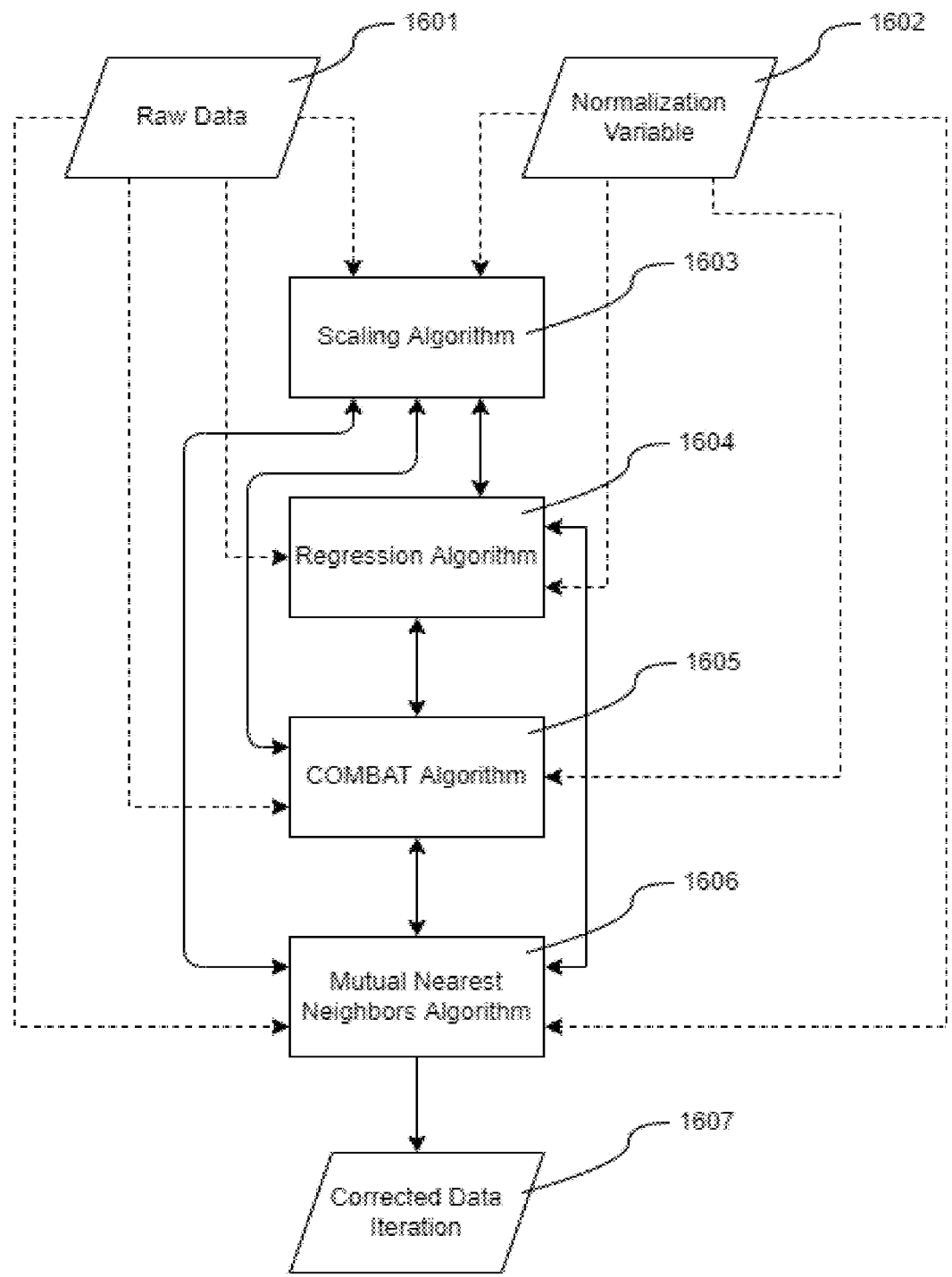
FIG. 15 is an exemplary iteration sequence of bias correction algorithms.
Figure 16:
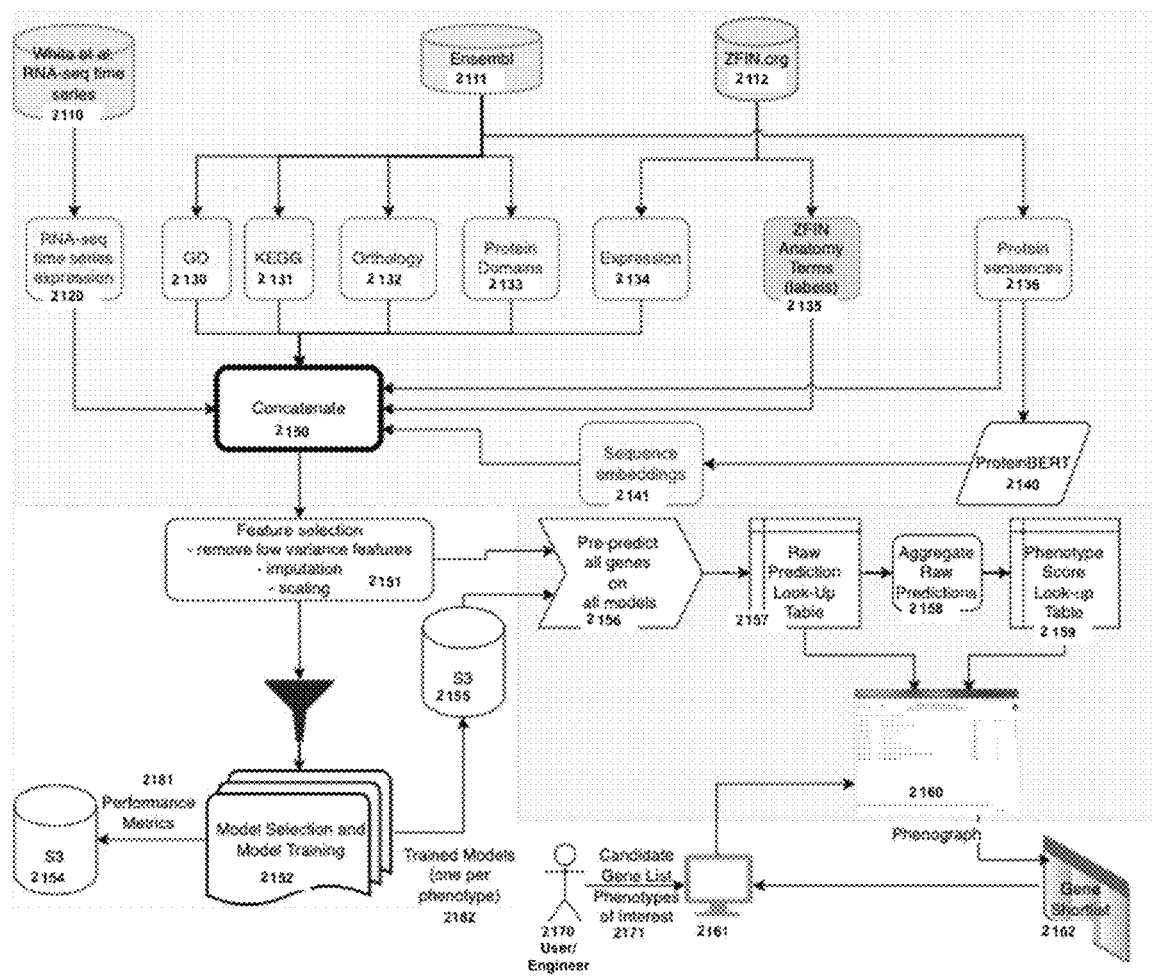
FIG. 16 is a diagram illustrating a method for Gene Disease Prioritization with use of a phenograph.
Figure 17:
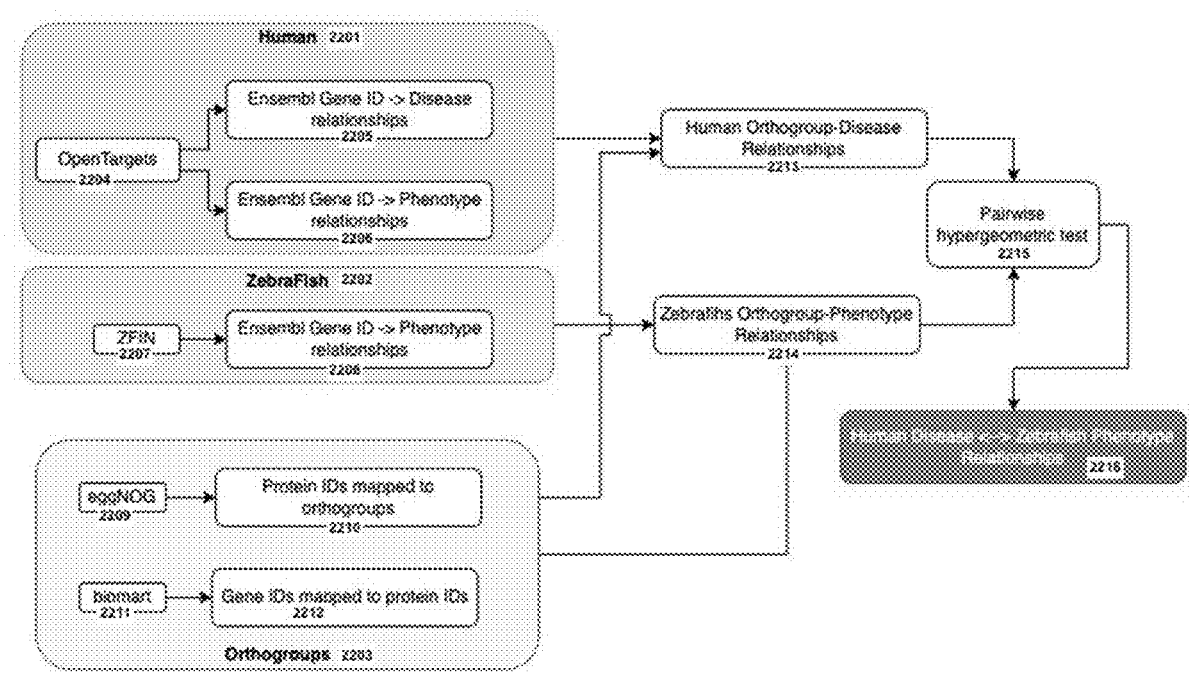
FIG. 17 is a diagram illustrating a method for producing human disease to zebrafish phenotype relationships.
Figure 18:
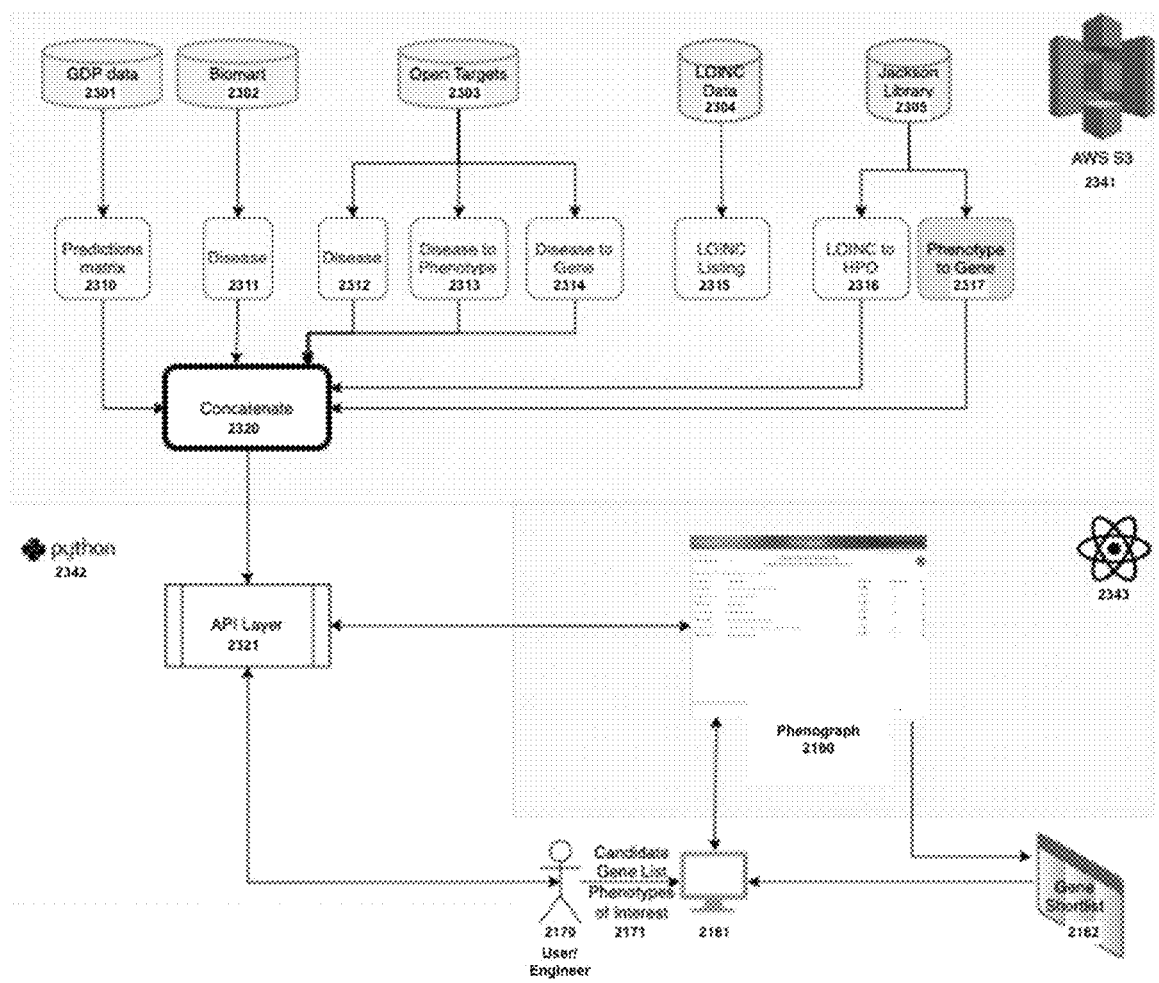
FIG. 18 is a diagram illustrating the connection of a feature matrix with an API layer that sends biological data to the phenograph.
Figure 19:
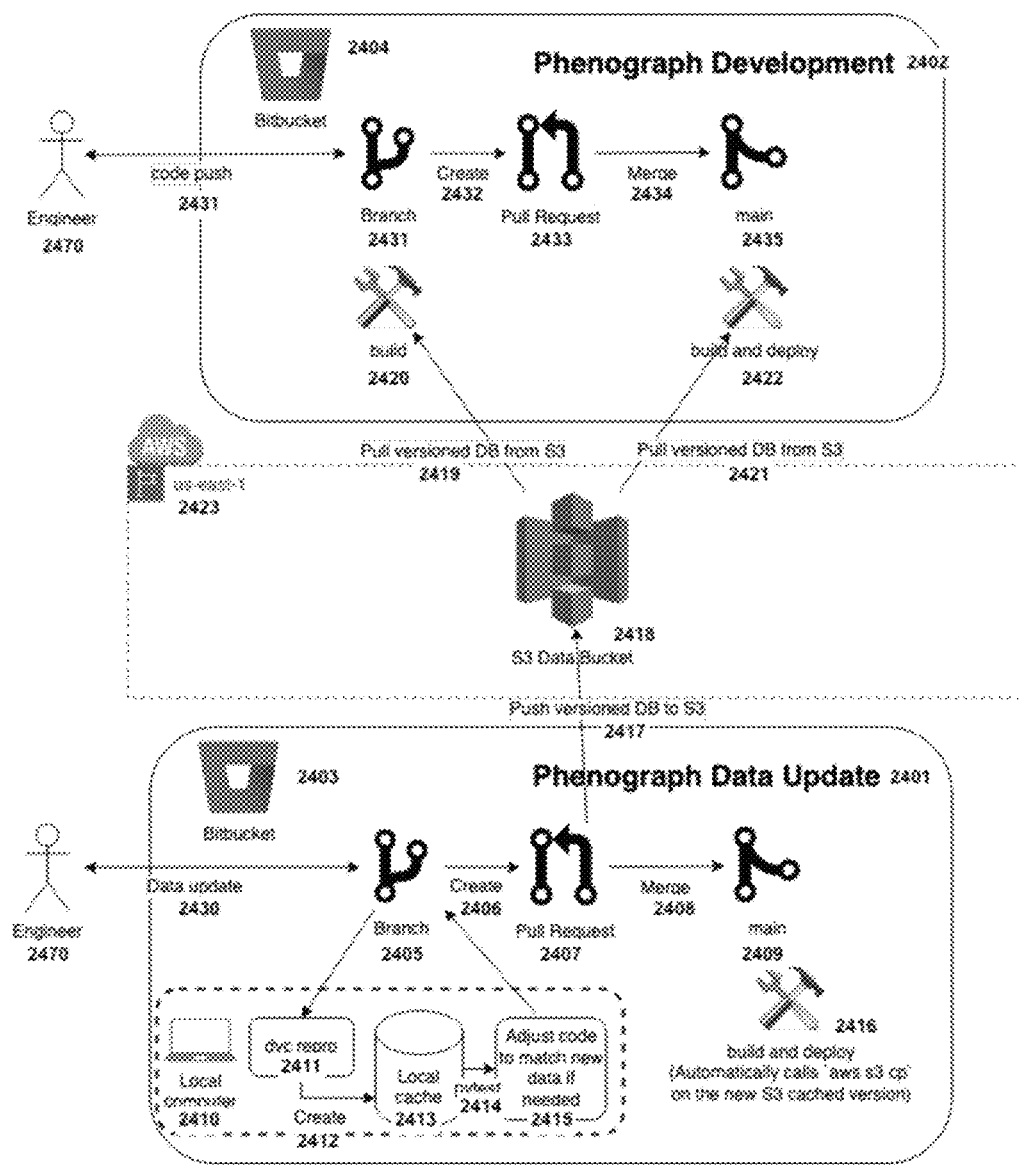
FIG. 19 is a diagram illustrating a method for creating and updating the phenograph development environment.
Figure 20:
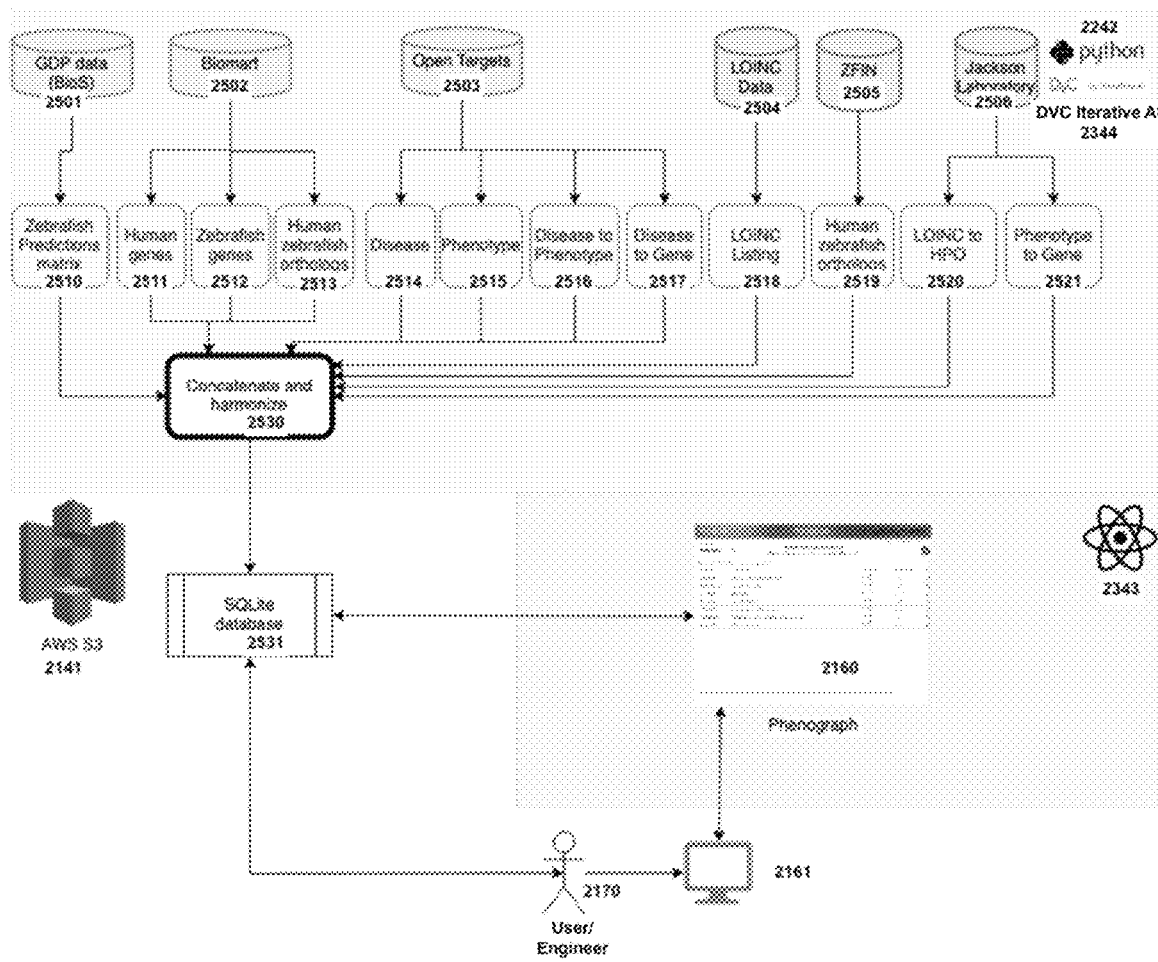
FIG. 20 is a diagram illustrating how the data is collected, harmonized, and stored in an SQLite database.
Figure 21:
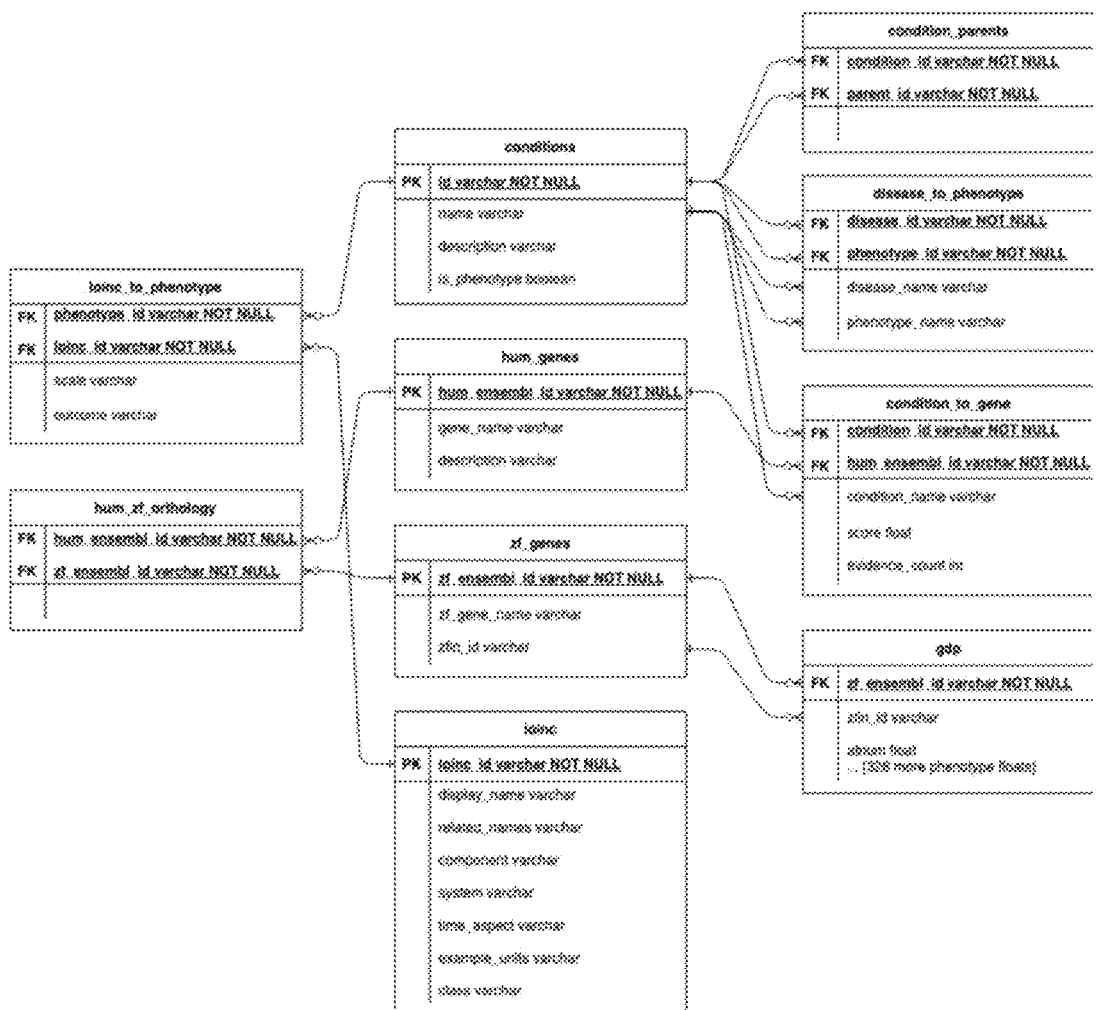
FIG. 21 is a depiction of the phenograph database schema.
Figure 22:
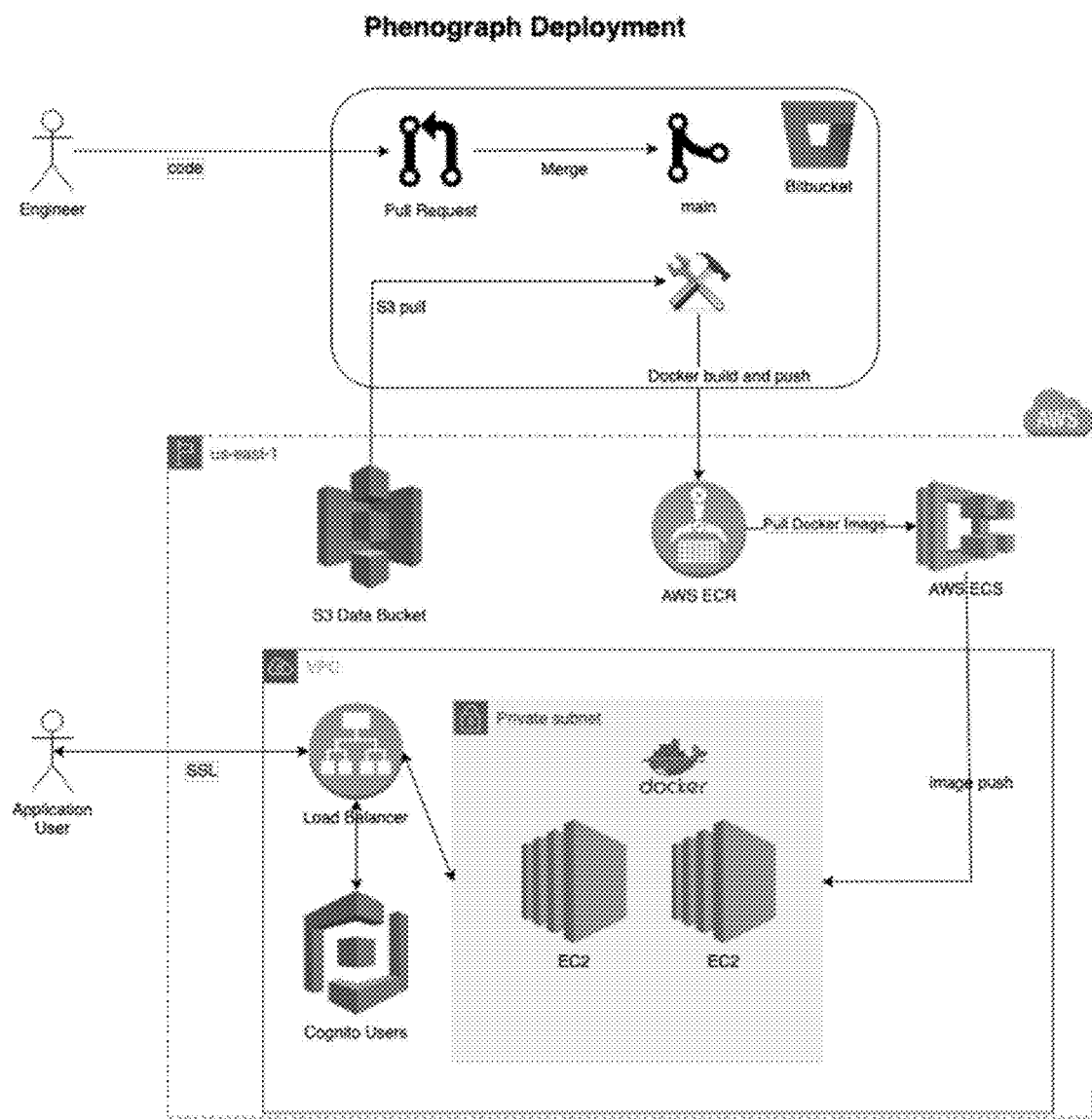
FIG. 22 is a diagram illustrating the phenograph deployment (deployed) environment architecture.
Figure 23:
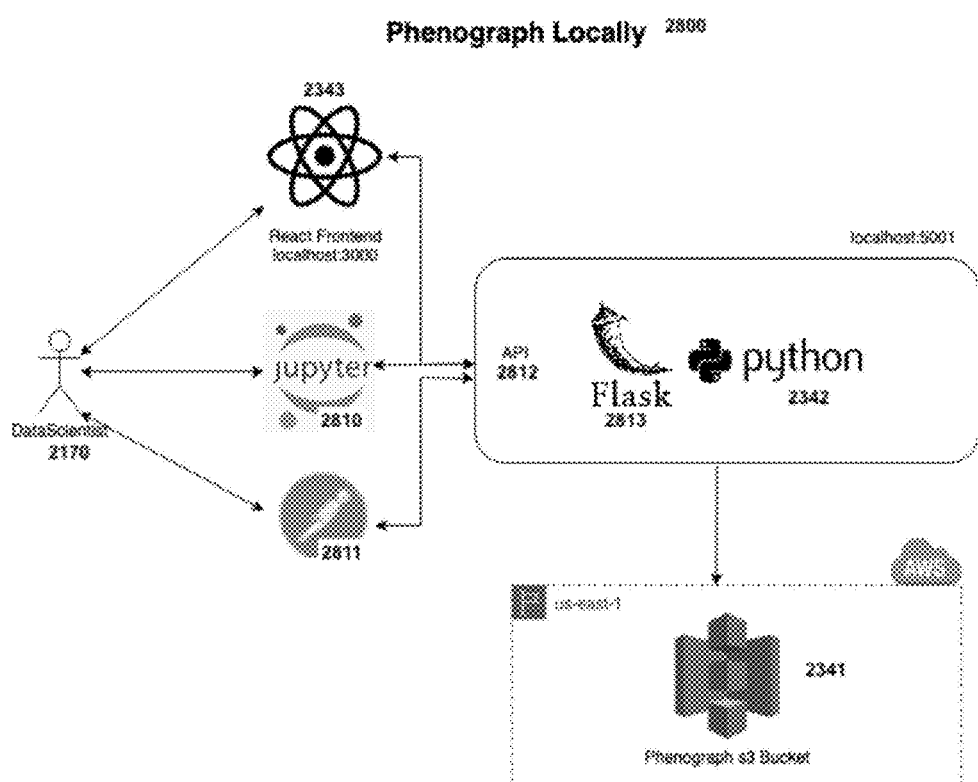
FIG. 23 is a diagram illustrating the phenograph local development environment architecture.
Figure 24:
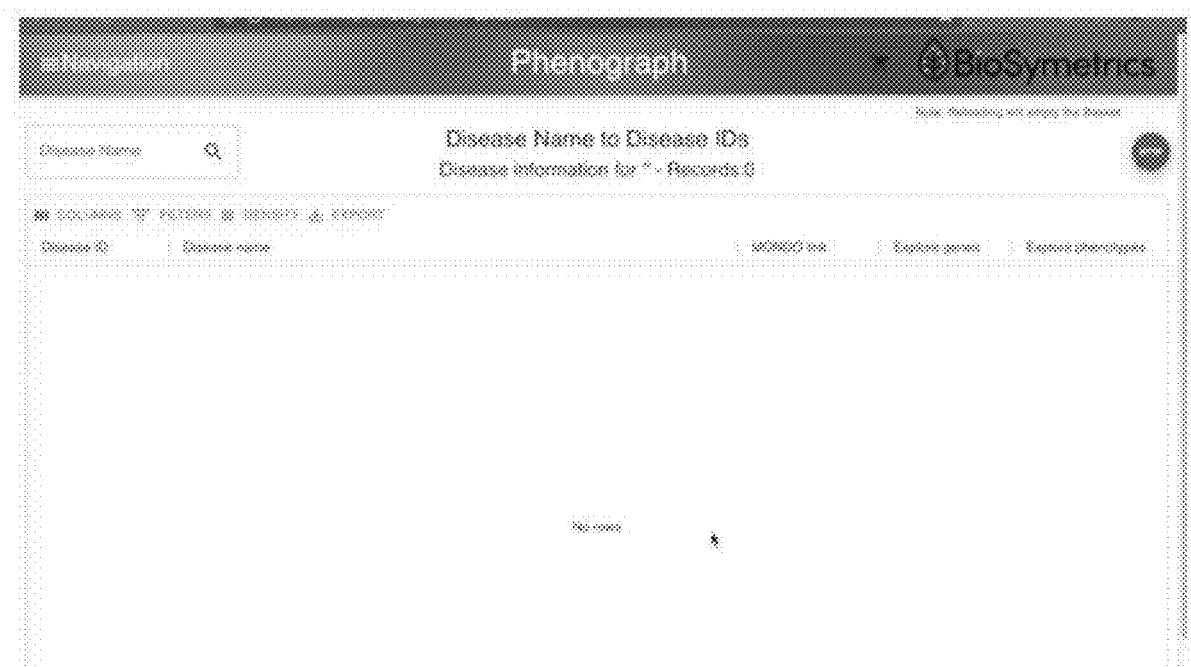
FIG. 24 is an image of the phenograph with the navigation tab, search bar, filters, and other features.
Figure 25:
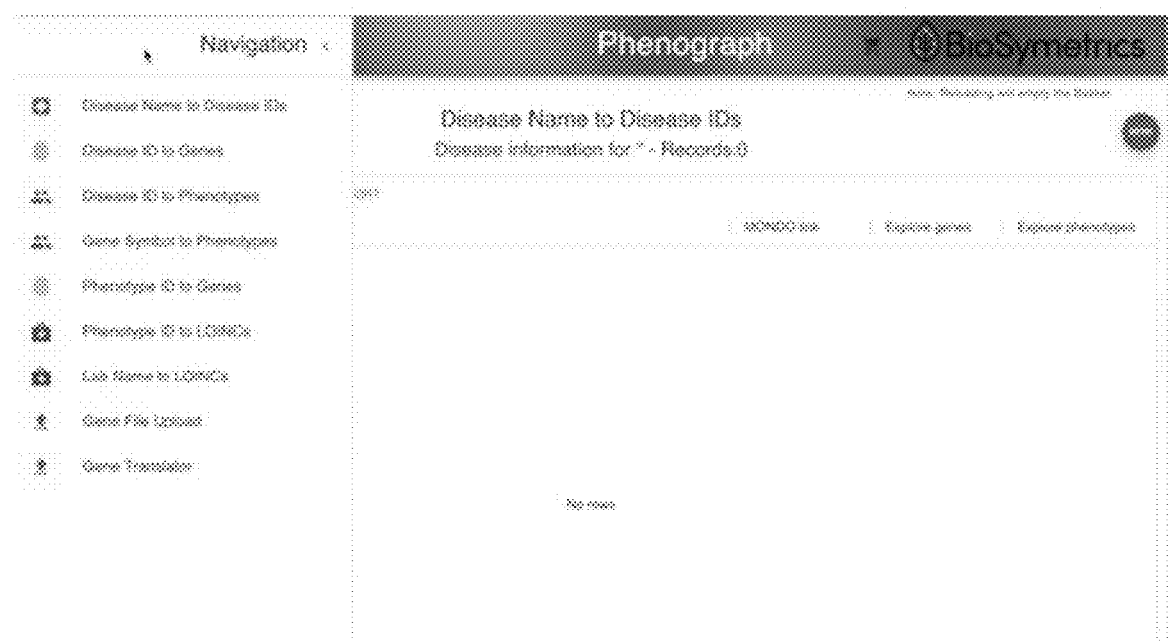
FIG. 25 is an image of the phenograph after the navigation tab is clicked.
Figure 26:
FIG. 26 is an image of the "Phenotype ID to Genes" page in the phenograph.
Figure 27:
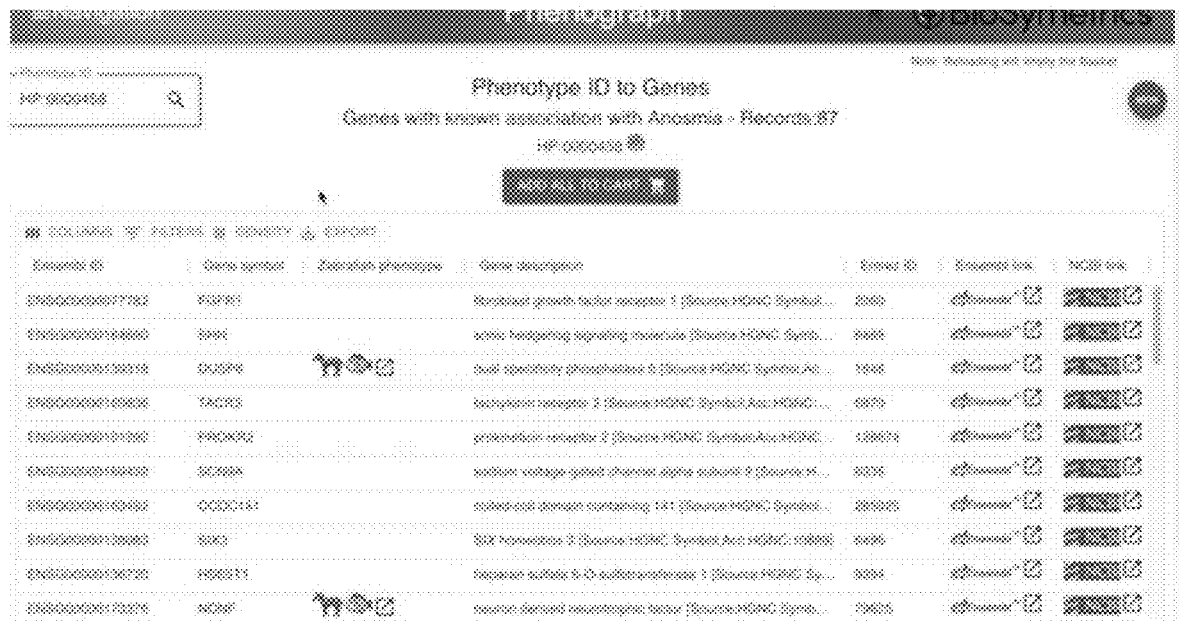
FIG. 27 is an image after searching for "HP:0000458" (anosmia) in the "Phenotype ID to Genes" search category.
Figure 28:
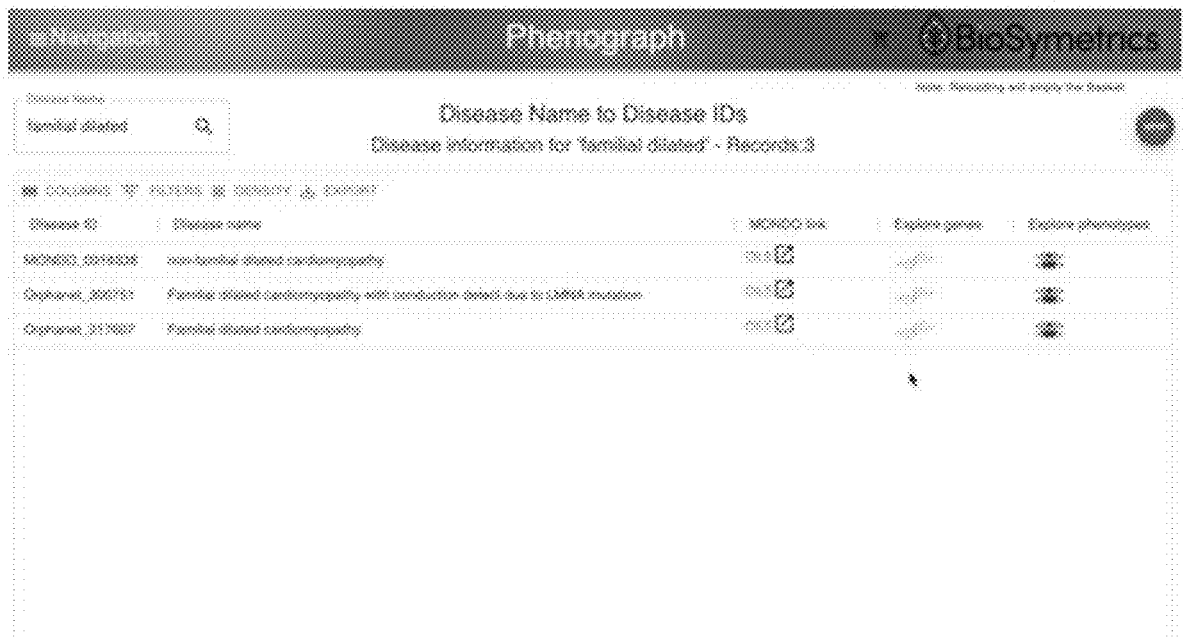
FIG. 28 is an image after searching for "familial dilated" in the "Disease Name to Disease IDs" search category.
Figure 29:
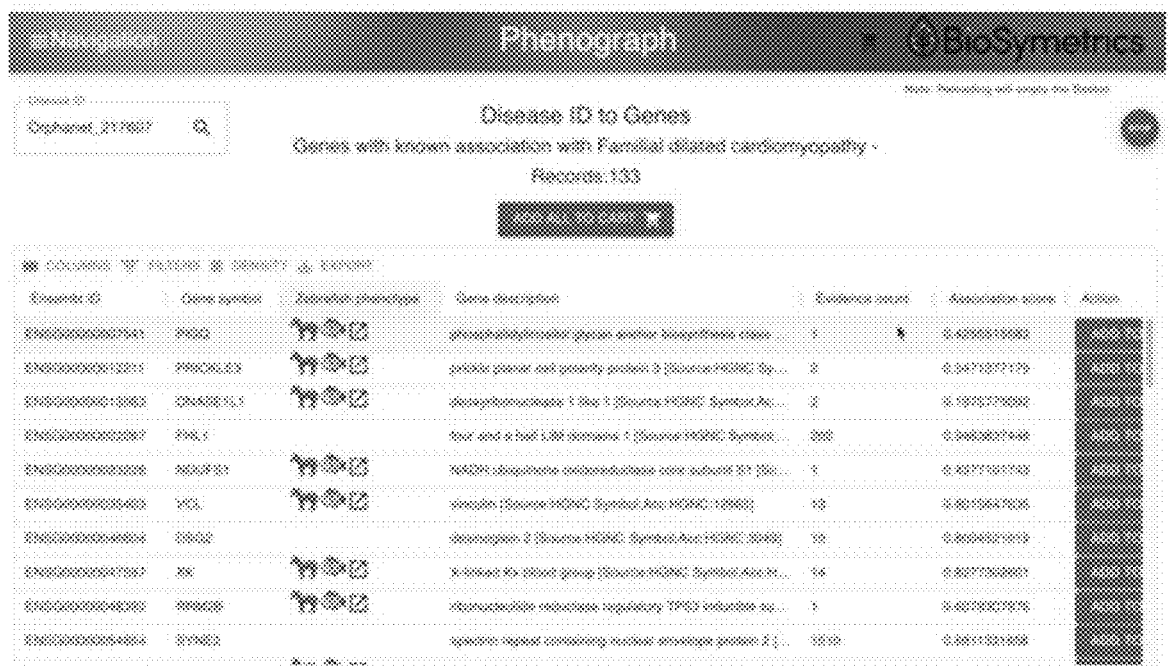
FIG. 29 is an image of the "Disease ID to Genes" page in the phenograph

FIG. 15 is an exemplary iteration sequence of bias correction algorithms. The raw data 1601 and the normalization variable 1602, which can be any one of a full data set, plate ID, batch ID, date of experiment, or any other known batch effect, are sent to any of the modules 1603 to 1606.

If they are sent to 1603, a scaling algorithm is used to normalize the raw data 1601 according to the normalization variable 1602. The scaling algorithm 1603 can be a simple linear scaling algorithm or can be slightly modified to be robust to outliers. An example of a robust scaling algorithm is the RobustScaler from the Sklearn python module. If the raw data 1601 and normalization variable 1602 are sent to module 1604, a regression algorithm is used to normalize the raw data 1601 according to the normalization variable 1602. The regression algorithm 1604 can be a simple linear regression algorithm or can be slightly modified to prevent overcorrection. If the raw data 1601 and normalization variable 1602 are sent to module 1605, a COMBAT algorithm is used to normalize the raw data 1601 according to the normalization variable 1602. The COMBAT algorithm is a "supervised" batch effect algorithm that requires the bias to be quantified before applying a linear Bayes method to remove the bias. If the raw data 1601 and normalization variable 1602 are sent to module 1606, a mutual nearest neighbors algorithm is used to normalize the raw data 1601 according to the normalization variable 1602. The mutual nearest neighbors algorithm uses a nonlinear correction that quantifies systematic differences between groups of similar cells and scales the rest of the cells in the batches using this information.

The raw data 1601 can be sent to any of the modules 1603 to 1606, however, the normalized data from one module can be sent to another module for normalization. For example, the raw data can be sent to module 1603 where it is normalized by a scaling algorithm. In most references, corrected batch cases will be requested to proceed with mosty scaling factor to set the mean to 0 with unit variance. However, outliers can often influence the sample mean in a negative way. In such cases, approach implemented is slightly modified to be robust with outliers.

This normalized data can be sent to module 1604, where the normalized data is again normalized, but this time by a regression algorithm. Regress out is a commonly used technique to address batch effects, particularly in single cell transcriptomics datasets. This is a particularly effective sequence when there is a need to normalize the data, perform variance stabilization and regress out the effects of any covariates that have an effect on our data.

This twice normalized data can be sent to module 1605 where it is normalized by a COMBAT algorithm. This is a particularly effective sequence to remove batch effects in microarray data. Non-biological experimental variation or "batch effects" are commonly observed across multiple batches of microarray experiments, often rendering the task of combining data from these batches difficult. The ability to combine microarray data sets is advantageous to researchers to increase statistical power to detect biological phenomena from studies where logistical considerations restrict sample size or in studies that require the sequential hybridization of arrays. Finally, the normalized data can be sent to module 1606 and normalized by a mutual nearest neighbors algorithm. The result of such a normalization procedure is a bias corrected data iteration.

There can be any combination of data normalizations. For example, the normalization procedure can start with the raw data 1601, which is sent to module 1605, from which the normalized data can be sent to module 1603, from which the normalized data can be sent to module 1604, from which the normalized data can be finally sent to module 1602, from which another bias corrected data iteration can be obtained. The parameters associated with each bias correction algorithm can also be changed to produce a bias corrected data iteration. The results of the full set of iterated normalization procedures and iterated bias correction parameters is contained within the corrected data iterations 1607.

Figure 14:
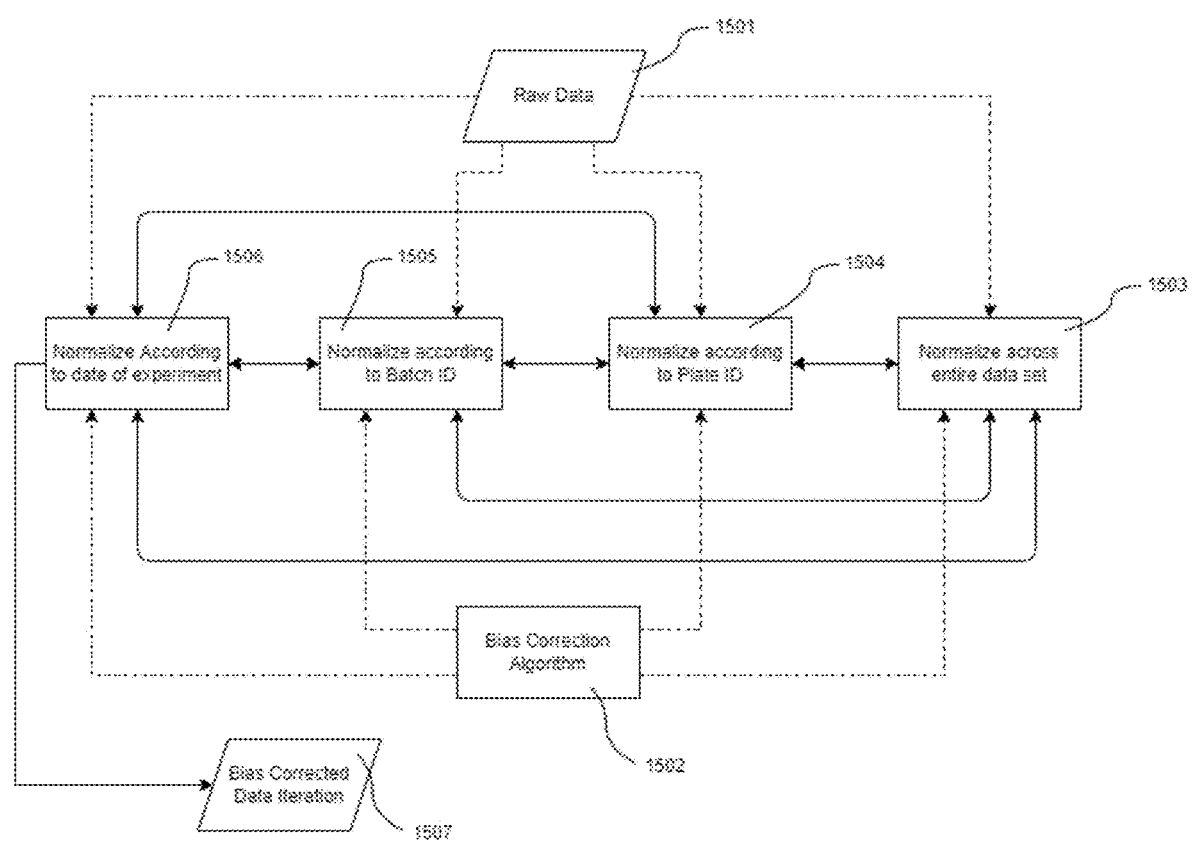
FIG. 14 is an exemplary bias correction iteration sequence for a single bias correction algorithm to normalize the data.

FIG. 14 is an exemplary bias correction iteration sequence for a single bias correction algorithm to normalize the data.

The raw data 1501 and the bias correction algorithm 1502, which could be any one of a scaling algorithm, regression algorithm, COMBAT algorithm, mutual nearest neighbors algorithm, or any other known batch effect correction algorithm, are sent to any of the modules 1503 to 1506.

If they are sent to 1503, the bias correction algorithm is used to normalize the data across the entire set. If they are sent to 1504, the bias correction algorithm is used to normalize the data according to the Plate ID, which is a type of batch effect, or nonbiological effect, originating from the small differences (sometimes microscopic differences) between cell culture plates. If they are sent to 1505, the bias correction algorithm is used to normalize the data according to the Batch ID, which is a type of batch effect originating from the small differences in cell batches. If they are sent to 1506, the bias correction algorithm is used to normalize the data according to the date that the experiment was conducted, which is another example of a batch effect.

The raw data 1501 can be sent to any of the modules 1503 to 1506, however, the normalized data from one module can be sent to another module for normalization. For example, the raw data can be sent to module 1503 where it is normalized across the entire data set. This normalized data can be sent to module 1504, where the normalized data is again normalized, but this time according to plate ID. This twice normalized data can be sent to module 1505 where it is normalized according to batch ID. Finally, the normalized data can be sent to module 1506 and normalized according to date of experiment. The result of such a normalization procedure is a bias corrected data iteration.

There can be any combination of data normalizations. For example, the normalization procedure can start with the raw data 1501, which is sent to module 1505, from which the normalized data can be sent to module 1503, from which the normalized data can be sent to module 1504, from which the normalized data can be finally sent to module 1502, from which another bias corrected data iteration can be obtained. The results of the full set of iterated normalization procedures is contained within the bias corrected data iterations 1507.

Now moving back to FIG. 10, there are several bias correction methods as explained above that are cooccurring in module 1017. Once the bias is detected, there are several steps the algorithm may apply to correct bias that are caused by the non-biological factors are causing. In most references, corrected batch cases will be requested to proceed with mosty scaling factor to set the mean to 0 with unit variance. This approach implemented is slightly modified to be robust with outliers. Regress out is a commonly used technique to address batch effects, particularly in single cell transcriptomics datasets.

These bias correction steps 1017 are then sent to the algorithm generator 1018 to be converted to a set of algorithms 1019. As in the preprocessing and feature selection loop, the set of algorithms 1019 are applied to the placeholder data 1014 in module 1020, generating a number of model predictions. The set of model predictions 1021 can also include nonbiological predictions, like the day of the week the data was gathered, or the name of the doctor or scientist that gathered the data. The model predictions 1021 as well as the data and bias info 1015 and the associated empirical results 1022 are sent to the module 1021. When these model predictions 1021 are sent to the module 1023, accurate biological predictions score high, while accurate nonbiological predictions score low, as the goal of the debiasing loop is to remove the ability to make nonbiological predictions.

The accuracy scores are then sent to the module 1013 which aims to find the parameters that produce the maximum difference in predictive ability between biological predictions and nonbiological predictions. In other words, the module 1013 aims to find the parameters that simultaneously produce the most accurate biological predictions and the least accurate nonbiological predictions. As this module was described before, the techniques used to find such parameters include random search and grid search hyperparameter optimization. The process repeats by looping back to the data placeholder module 1014 and applying different bias correction algorithms, thereby generating different accuracy scores for each set of algorithms.

As explained above, there are two aspects to bias reduction: 1) using multiple approaches (scaling, regression, COMBAT, MNN) to attempt to remove non-biological signal, and then evaluating the effectiveness of these approaches using an ML framework. It is difficult to measure the effect of these de-biasing methods until the very end of the ML process. There, we examine the performance of a "true" model that looks to predict the outcome of interest, and a "bias" model, that looks to predict a non-biological feature of the data (e.g. survey date, surveyor, batch). What optimize for best performance of the "true" model, and worst performance of the "bias" model.

Once the module 1013 converges on the desired preprocessing, feature selection, and bias correction parameters, the information about the highest scoring parameters is sent to module 1024, where a user can either choose to select a set of preprocessing steps according to the accuracy scores and information about the application of the algorithms, such as speed or computational requirements, or to allow the algorithms to be automatically selected based on a chosen specialty, like highest speed algorithm, or most accurate algorithm. If more than one permutation is selected, the selected permutations may be displayed as options to the user. The outputs of this process are the selected algorithms 1025, which can then be applied to data to make predictions without the need for empirical validation.

The training module can utilize a machine learning algorithm or other algorithm to construct and train an assessment model to be used in the diagnostic tests, for example. An assessment model can be constructed to capture, based on the training data, the statistical relationship, if any, between a given feature value and a specific developmental disorder to be screened by the diagnostic tests. The assessment model may, for example, comprise the statistical correlations between a plurality of clinical characteristics and clinical diagnoses of one or more genetic, neurological, behavioral or mental health disorders.

A given feature value may have a different predictive utility for classifying each of the plurality of genetic, neurological, behavioral or mental health disorders to be evaluated in the diagnostic tests. The machine learning algorithm can be used to extract these statistical relationships from the training data and build an assessment model that can yield an accurate prediction of a develop mental disorder when a dataset comprising one or more feature values is fitted to the model.

In some instances, the diagnosis module can comprise data processing module as described herein. The data processing module can enable the diagnosis module to provide an assessment on the subject with reduced number of test questions. The data processing module can comprise a preprocessing module, a training module and a prediction module as described herein. The data processing module can extract training data from a database or a user, apply one or more transformations to standardize the training data and pass the standardized training data to the training module.

The training module can utilize a machine learning algorithm or other algorithm to construct and train an assessment model to be used in the diagnostic tests, based on the standardized training data. Once an assessment model is derived from the training data, the model may be used as a prediction tool to assess the risk of a subject for cognitive function such as developmental advancement, or one or more disorders such as behavioral, neurological or mental health disorders. The training data can comprise data developed on a population where the subject patient is not a member of the population. The prediction module can be configured to generate a predicted classification of cognitive function (e.g., developmental disorder) of a given subject, by fitting new data to an assessment model constructed in the training module. The data processing module can identify a most predictive next question based on a plurality of answers to a plurality of asked questions, as discussed herein, such that a person can be diagnosed or identified as at risk and treated with fewer questions.

One or more machine learning algorithms may be used to construct the assessment model, such as support vector machines that deploy stepwise backwards feature selection and/or graphical models, both of which can have advantages of inferring interactions between features.

For example, machine learning algorithms or other statistical algorithms may be used, such as alternating decision trees (ADTree), Decision Stumps, functional trees (FT), logistic model trees (LMT), logistic regression, Random Forests, linear classifiers, or any machine learning algorithm or statistical algorithm known in the art.

One or more algorithms may be used together to generate an ensemble method, wherein the ensemble method may be optimized using a machine learning ensemble meta-algorithm such as a boosting (e.g., AdaBoost, LPBoost, Tota!Boost, BrownBoost, MadaBoost, LogitBoost, etc.) to reduce bias and/or variance. Once an assessment model is derived from the training data, the model may be used as a prediction tool to assess the risk of a subject for having one or more behavioral, neurological or mental health disorders.

Machine learning analyses may be performed using one or more of many programming languages and platforms known in the art, such as R, Weka, Python, and/or Matlab, for example.

The training module may comprise feature selection. One or more feature selection algorithms (such as support vector machine, convolutional neural nets) may be used to select features able to differentiate between individuals with and without certain behavioral, neurological or mental health disorders. Different sets of features may be selected as relevant for the identification of different disorders. Stepwise backwards algorithms may be used along with other algorithms. The feature selection procedure may include a determination of an optimal number of features.

The training module may be configured to evaluate the performance of the derived assessment models. For example, the accuracy, sensitivity, and specificity of the model in classifying data can be evaluated. The evaluation can be used as a guideline in selecting suitable machine learning algorithms or parameters thereof. The training module can thus update and/or refine the derived assessment model to maximize the specificity (the true negative rate) over sensitivity (the true positive rate). Such optimization may be particularly helpful when class imbalance or sample bias exists in training data.

In at least some instances, available training data may be skewed towards individuals diagnosed with a specific disorder. In such instances, the training data may produce an assessment model reflecting that sample bias, such that the model assumes that subjects are at risk for the specific developmental disorder unless there is a strong case to be made otherwise. An assessment model incorporating such a particular sample bias can have less than ideal performance in generating predictions of new or unclassified data, since the new data may be drawn from a subject population which may not comprise a sample bias similar to that present in the training data.

To further reduce the contribution of training data sample bias to the generation of an assessment model, a boosting technique may be implemented during the training process. Boosting comprises an iterative process, wherein after one iteration of training, the weighting of each sample data point is updated. For example, samples that are misclassified after the iteration can be updated with higher significances. The training process may then be repeated with the updated weightings for the training data.

Some embodiments with a predictive modeling system include a predictive modeling exploration engine, a user interface, a library of predictive modeling techniques, and a predictive model deployment engine. The exploration engine may implement a search technique (or "modeling methodology") for efficiently exploring the predictive modeling search space (e.g., potential combinations of pre-processing steps, modeling algorithms, and post-processing steps) to generate a predictive modeling solution suitable for a specified prediction problem.

The search technique may include an initial evaluation of which predictive modeling techniques are likely to provide suitable solutions for the prediction problem. In some embodiments, the search technique includes an incremental evaluation of the search space (e.g., using increasing fractions of a dataset), and a consistent comparison of the suitability of different modeling solutions for the prediction problem (e.g., using consistent metrics). In some embodiments, the search technique adapts based on results of prior searches, which can improve the effectiveness of the search technique over time.

The exploration engine may use the library of modeling techniques to evaluate potential modeling solutions in the search space. In some embodiments, the modeling technique library includes machine-executable templates encoding complete modeling techniques. A machine-executable template may include one or more predictive modeling algorithms. In some embodiments, the modeling algorithms included in a template may be related in some way. For example, the modeling algorithms may be variants of the same modeling algorithm or members of a family of modeling algorithms. In some embodiments, a machine-executable template further includes one or more pre-processing and/or post-processing steps suitable for use with the template's algorithm(s). The algorithm(s), preprocessing steps, and/or post-processing steps may be parameterized. A machine-executable template may be applied to a user dataset to generate potential predictive modeling solutions for the prediction problem represented by the dataset.

Library of predictive modeling techniques includes machine-executable templates encoding complete predictive modeling techniques. In some embodiments, a machine-executable template includes one or more predictive modeling algorithms, zero or more pre-processing steps suitable for use with the algorithm(s), and zero or more post-processing steps suitable for use with the algorithm(s). The algorithm(s), pre-processing steps, and/or post-processing steps may be parameterized. A machine-executable template may be applied to a dataset to generate potential predictive modeling solutions for the prediction problem represented by the dataset.

A template may encode, for machine execution, pre-processing steps, model-fitting steps, and/or post-processing steps suitable for use with the template's predictive modeling algorithm(s). Examples of pre-processing steps include, without limitation, imputing missing values, feature engineering (e.g., one-hot encoding, splines, text mining, etc.), feature selection (e.g., dropping uninformative features, dropping highly correlated features, replacing original features by top principal components, etc.). Examples of model-fitting steps include, without limitation, algorithm selection, parameter estimation, hyper-parameter tuning, scoring, diagnostics, etc. Examples of post-processing steps include, without limitation, calibration of predictions, censoring, blending, etc.

(9) Use of a Cloud Network for Data Preprocessing

A cloud network allows for an application and data to be stored in a location other than the user's personal computing device. The application and associated data are instead stored in a computer system, in this case a parallel computing network, that is owned and operated by the cloud provider. A cloud network allows for a shared and organized database, which can be considered a proprietary piece or set of pieces of physical equipment.

The database can draw from public sources on the internet, private data streams from hospitals and healthcare providers, academic sources, and can even be expanded by a multitude of users that have access to local data. If the users can add local data to the shared database, the other users will be benefited by greater access to information and the machine learning algorithms will be made more accurate by the additional opportunity for refinement.

The machine learning algorithms can be constantly updated over a cloud network, so that the user does not need to use a personal machine to access a database and refine the software itself every time it needs to be updated. Since the cloud network allows the user access to remote computing resources, it can also connect the user to a remote parallel computing network that is owned and operated by the cloud service provider. Multiple users can connect to the parallel computing network at the same time. If multiple users that are connected to the parallel computing network at the same time desire the completion of common tasks, the network only needs to complete the task once, decreasing the computing resources required.

This is beneficial to both the cloud service provider, as fewer resources are needed, and also beneficial to users that request tasks that have been recently requested and completed by a different user. A cloud network also allows for the cloud service provider to gather data and statistics about the use of its software and the requirements of the users. This data can not only be used by the cloud service provider to allocate computing resources, but also to allocate business resources. Overall, a cloud network makes the ML preprocessing algorithm refinement faster and more immediate, as well as granting easier and faster access to users.

Figure 11:
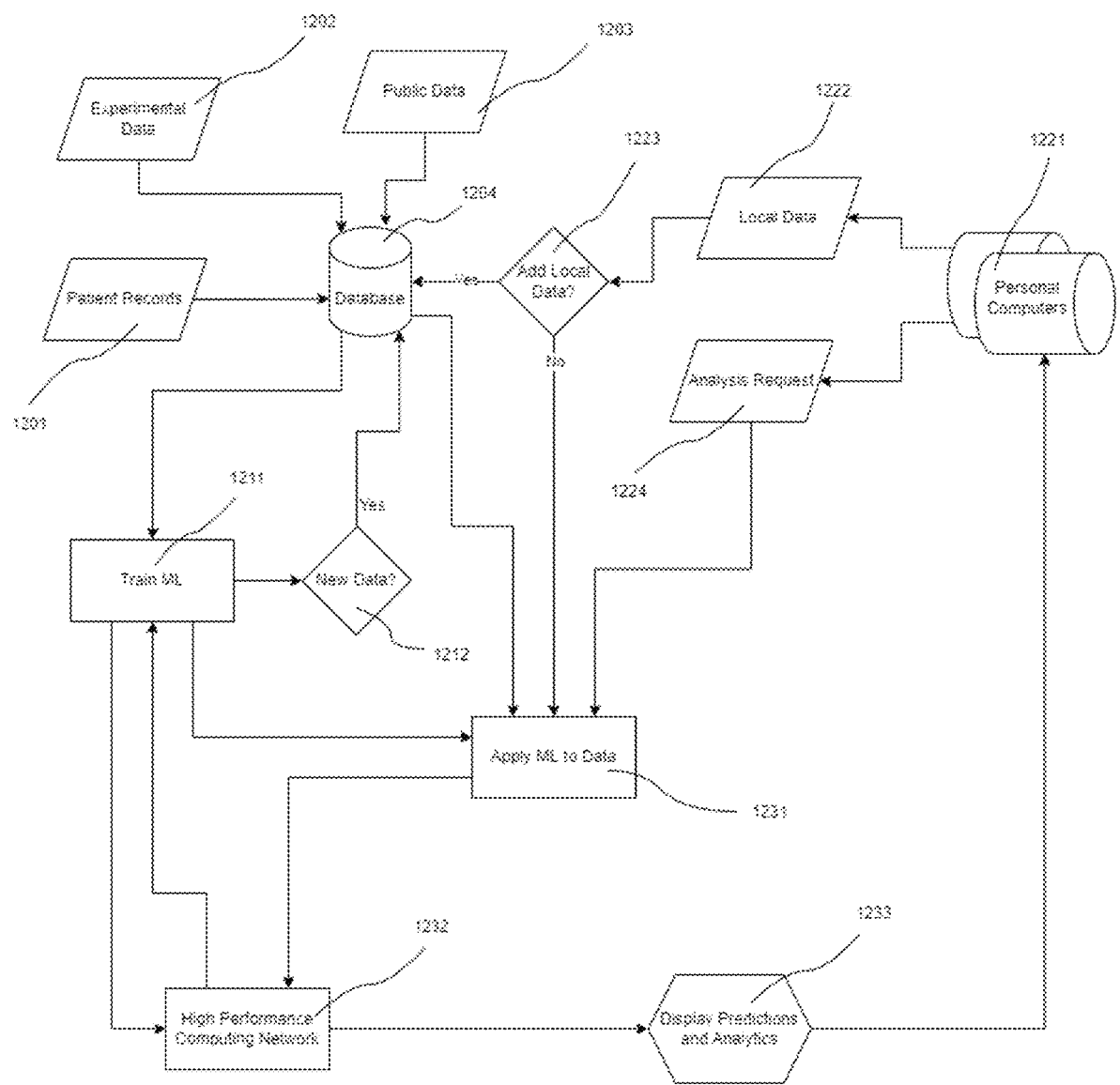
FIG. 11 is a flow diagram of an exemplary process of integrating heterogeneous datasets for ML predictive model creation.

FIG. 11 is related to an exemplary process of utilizing cloud computing to enable data pre-processing, specifically in biomedical predictive model creation.

In FIG. 11, various types of biomedical data are gathered from healthcare providers and hospitals (1201), laboratories and academic journals (1202), and public internet databases (1203) and stored in a central database 1204 that is connected to the cloud network. The type of data could be anything relevant to the creation of a predictive model, but some examples are Magnetic Resonance Imaging (MRI), functional Magnetic Resonance Imaging (fMRI) data, an Electroencephalogram (EEG) data, an Electrocardiogram (EKG/ECG) data, a genetics data, a proteomics data, data from wearable devices, an Electronic Health Record (EHR) data, and Electronic Medical Record (EMR) data, Chemical Structures (SMILES, InCHI, SDF), Images (PNG, JPEG), including from pathology or other applications of microscopy, and other healthcare and medical research related data options.

Relevant data is used to train a machine learning engine 1211. The decision module 1212 represents a constant update loop, which checks if any new data is available in the database to be used to train the machine learning algorithm and updates the algorithm accordingly. The process of training the machine learning algorithm can be accomplished by a high performance computing network 1232 that is owned and operated by the cloud service provider. A group of personal computers 1221, which are simultaneously connected to the cloud network, can send local data 1222 or set of tasks 1224 to the cloud network. The set of tasks contains all of the necessary information, apart from biomedical data, for the analysis to take place, including which data to gather from the database, the type of predictive model required, and the type of analysis to run on the quantitative prediction results.

The user can also specify in the tasks module whether they would like to use an existing trained machine learning algorithm or to train a new machine learning algorithm from a specific dataset. The local data 1222 can be added to the biomedical database for access by other users, or be sent straight to the machine learning algorithm 1231 so that the data remains private, represented by a decision module 1223. The machine learning engine then gathers the local data or shared data from the database as well as the requests from the users, and applies the chosen machine learning algorithm 1211 to the data. The process of applying the machine learning algorithm to the data and the analysis of the results can be accomplished by a high performance computing network 1232 that is owned and operated by the cloud service provider. The predictive results and analyses 1233 are sent back to the personal computers so that they can be visually displayed to the users.

All data will be automatically sent to the cloud storage system. All data sent and stored in the cloud platform will be stored anonymously. No personal identifying information will be stored and patients will be assigned a numeric-alpha patient identifier code. In addition the cloud platform will include a set of visualization tools such as interactive charts and plots of the evolution of the monitored data over time to provide a greater amount of information.

All data will automatically be stored in a secure cloud storage platform. As soon as patient and user profiles are created, all personal information will be anonymized and only accessible to appropriate parties in password protected archive records.

The storage system is coupled to the cloud services provider via a data communications link. The data communications link may be embodied as a dedicated data communications link, as a data communications pathway that is provided through the use of one or data communications networks such as a wide area network ('WAN') or local area network ('LAN'), or as some other mechanism capable of transporting digital information between the storage system and the cloud services provider. Such a data communications link may be fully wired, fully wireless, or some aggregation of wired and wireless data communications pathways.

In such an example, digital information may be exchanged between the storage system and the cloud services provider via the data communications link using one or more data communications protocols. For example, digital information may be exchanged between the storage system and the cloud services provider via the data communications link using the handheld device transfer protocol ('HDTP'), hypertext transfer protocol ('HTTP'), internet protocol ('IP'), real-time transfer protocol ('RTP'), transmission control protocol ('TCP'), user datagram protocol ('UDP'), wireless application protocol ('WAP'), or other protocol.

The cloud services provider may be embodied, for example, as a system and computing environment that provides services to users of the cloud services provider through the sharing of computing resources via the data communications link. The cloud services provider may provide on-demand access to a shared pool of configurable computing resources such as computer networks, servers, storage, applications and services, and so on. The shared pool of configurable resources may be rapidly provisioned and released to a user of the cloud services provider with minimal management effort.

Generally, the user of the cloud services provider is unaware of the exact computing resources utilized by the cloud services provider to provide the services. Although in many cases such a cloud services provider may be accessible via the Internet, readers of skill in the art will recognize that any system that abstracts the use of shared resources to provide services to a user through any data communications link may be considered a cloud services provider.

The cloud services provider may be configured to provide a variety of services to the storage system and users of the storage system through the implementation of various service models. For example, the cloud services provider may be configured to provide services to the storage system and users of the storage system through the implementation of an infrastructure as a service ('IaaS') service model where the cloud services provider offers computing infrastructure such as virtual machines and other resources as a service to subscribers. In addition, the cloud services provider may be configured to provide services to the storage system and users of the storage system through the implementation of a platform as a service ('PaaS') service model where the cloud services provider offers a development environment to application developers.

Such a development environment may include, for example, an operating system, programming-language execution environment, database, web server, or other components that may be utilized by application developers to develop and run software solutions on a cloud platform.

Furthermore, the cloud services provider may be configured to provide services to the storage system and users of the storage system through the implementation of a software as a service ('SaaS') service model where the cloud services provider offers application software, databases, as well as the platforms that are used to run the applications to the storage system and users of the storage system, providing the storage system and users of the storage system with on-demand software and eliminating the need to install and run the application on local computers, which may simplify maintenance and support of the application.

The cloud services provider may be further configured to provide services to the storage system and users of the storage system through the implementation of an authentication as a service ('AaaS') service model where the cloud services provider offers authentication services that can be used to secure access to applications, data sources, or other resources.

The cloud services provider may also be configured to provide services to the storage system and users of the storage system through the implementation of a storage as a service model where the cloud services provider offers access to its storage infrastructure for use by the storage system and users of the storage system.

Cloud migration tools may also be configured to address potentially high network costs and long transfer times associated with migrating large volumes of data to the cloud services provider, as well as addressing security concerns associated with sensitive data to the cloud services provider over data communications networks. In order to further enable the storage system and users of the storage system to make use of the services provided by that may be offered by the cloud services provider or a limitation as to the service models that may be implemented by the cloud services provider.

(10) Use of Parallel Computing Cloud Network for Data Preprocessing

Using a parallel computing network to create and run a predictive model is technically more difficult, but superior in many areas to using a singular instance of a program on one machine to accomplish the same goal. An API is used to connect a user to a parallel computing network, and to connect a parallel computing network to a database. The parallel computing network receives tasks from the user and executes the tasks while accessing the designated data from the database, sending the results back to the user.

The tasks can include variation of preprocessing steps and parameters, execution of preprocessing steps, feature selection, and machine learning model creation and training. The algorithms used to execute the tasks can be parallelized to allow for faster completion of tasks and more balanced usage of computing resources. For example, if the required task is matrix multiplication, instead of using a traditional sequential algorithm, the parallel computing network can use a divide-and-conquer algorithm such as a Strassen algorithm on multiple processors to significantly speed up the completion of the task.

Parallelizing sequential algorithms is not a simple task and its difficulty or possibility is completely dependent on the algorithm. Aside from algorithmic parallelization, machine learning model training can also be parallelized.

Figure 12:
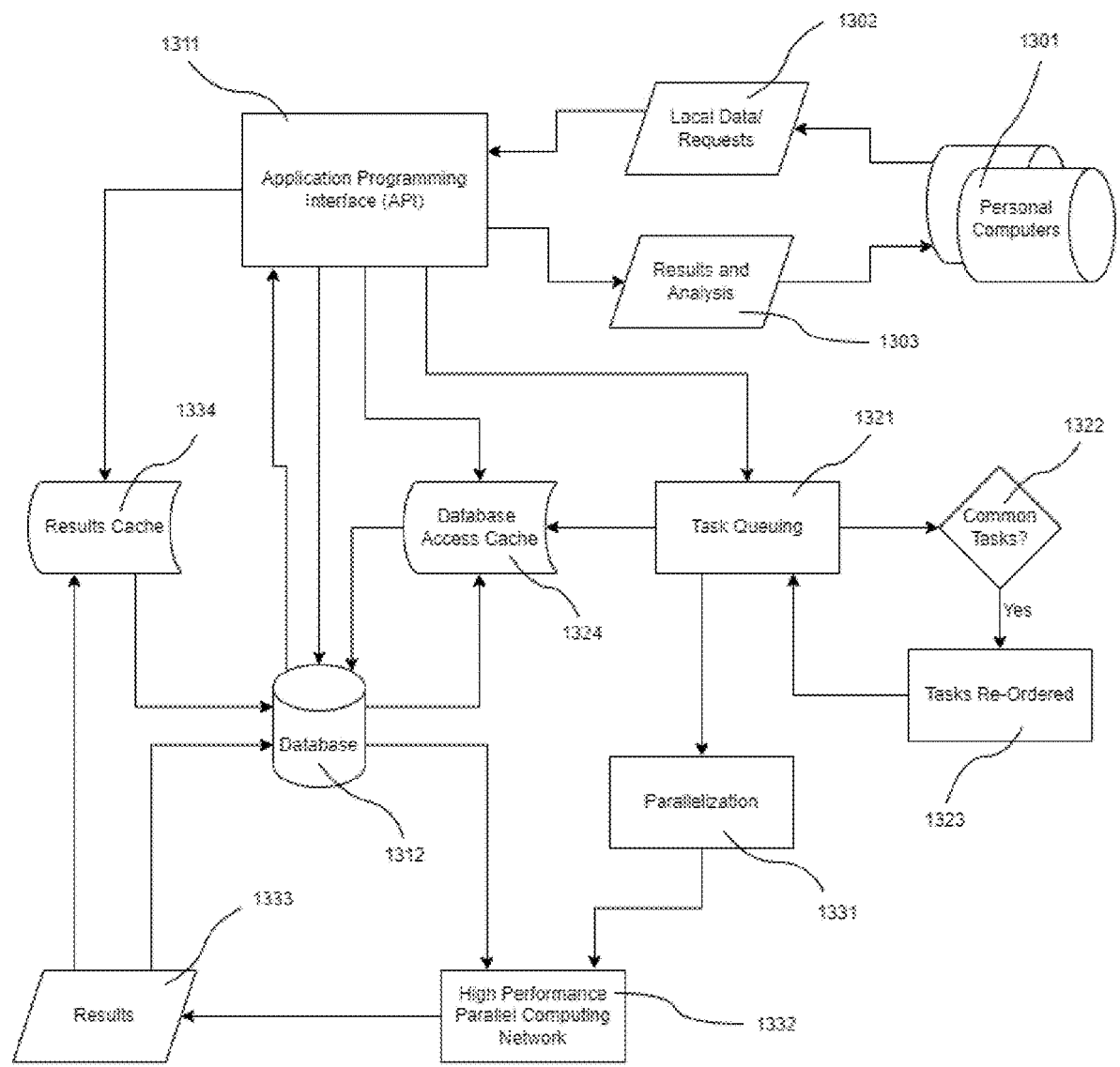
FIG. 12 is a flow diagram of an exemplary process for using a cloud network for data preprocessing specifically in biomedical predictive model creation.

FIG. 12 is related to an exemplary process for using parallel computing networks and associated API specifically for data preprocessing, specifically for biomedical predictive model creation over a cloud network.

Now referring to FIG. 12, the personal computers 1301 send local data and requests 1302 to the API 1311. The local data is sent to a remote database 1312 and the caching engine 1324 stores information about how to access the data quickly. The requests are sent to the task queuing engine 1321. The tasks can include variation of preprocessing steps and parameters, execution of preprocessing steps, feature selection, or machine learning algorithm, machine learning model creation and training, and retrieving data or results from a database. The decision module 1322 searches the task queue for common or similar tasks and 1323 reorders the queue so that the same task does not need to be completed repeatedly.

The first task in the queue is sent to the parallelization module 1331, which decides how to parallelize the task. If the task were a simple data transformation, like a matrix multiplication process, a suitable parallel method would be selected to complete the task in a parallel computing framework. For the example of matrix multiplication, instead of using a traditional sequential algorithm, the parallel computing network can use a divide-and-conquer algorithm such as a Strassen algorithm on multiple processors to significantly speed up the completion of the task.

If the task were the execution of a machine learning training process, the parallelization module could select one of two methods, data parallelism or model parallelism. If the parallelization module selects data parallelism, the same machine learning model is trained on different processors by dividing the training data and sending each data division to a separate instance of the same machine learning algorithm. If the parallelization module selects model parallelism, the machine learning model itself is divided into different layers to be trained on the same data set. If the first task in the queue involves retrieving data from the database, it is sent to the caching engine 1324 to speed the retrieval. The data from the database, along with the parallelization instructions, are sent to the high-performance parallel computing network 1332.

The results of the computations 1333 are sent to the database for storage, and the storage information is sent to the results cache 1334, so that users looking for results in the database can be found easily. The results can include prediction quantities, accuracy scores, preprocessing algorithms, preprocessing parameter values, and computational information like required resources or computation time.

If a user request from module 1302 received by the API 1311 is the retrieval of results, the result cache 1334 assists the API to find them in the database 1312. The results are then sent from the database to the API. If the analysis of the data requires more high performance computing, the necessary analysis algorithms are sent to the task queue to be sent to the parallel computing network.

The API then retrieves the results and analysis 1303 and sends them to the desired personal computers on the cloud network. If the data analysis only requires minimal computing power, the API sends the raw data to the personal computers so that they can analyze the data independently. If the user only desires to access and analyze data from the database, the API can directly access the database cache and retrieve raw data from the database to send to the user.

Data transmission network may also include one or more cloud networks. Cloud network may include a cloud infrastructure system that provides cloud services. In certain embodiments, services provided by the cloud network may include a host of services that are made available to users of the cloud infrastructure system on-demand. Cloud network is shown as being connected to computing environment (and therefore having computing environment as its client or user), but cloud network may be connected to or utilized by any of the devices.

Services provided by the cloud network can dynamically scale to meet the needs of its users. The cloud network may comprise one or more computers, servers, and/or systems.

In some embodiments, the computers, servers, and/or systems that make up the cloud network are different from the user's own on-premises computers, servers, and/or systems. For example, the cloud network may host an application, and a user may, via a communication network such as the Internet, on-demand, order and use the application.

Using parallel computing network and allowing transportation of a model between users of the platform carries great significance. However, protecting molecular structures from disclosure against external parties also carries prominence in this framework.

In some embodiments, the process may require the algorithmic model to directly ingest and process chemical structure information, which can be sensitive and proprietary data.

Securely exchanging chemical data without revealing the molecular structure is of great importance, as sharing data such as fingerprints and measured endpoints between research groups within industry through collaboration is often accomplished to improve drug discovery.

It is common in pharmaceutical and biomolecular industries to exchange datasets by encoding the molecular structures into descriptors. Molecular fingerprints such as the extended-connectivity fingerprints (ECFPs) are frequently used for such an exchange, because they typically perform well on quantitative structure-activity relationship tasks.

The ECFP representation is a refinement of the Morgan algorithm and usually hashed and folded into a fixed size 1024, 2048 or 4096 sparse bit or count vector to further utilize for predictive modeling tasks. During the fingerprint creation, the ECFP algorithm considers the atom environment, based on the maximum number of atomic neighbors, i.e. bond diameter d, and iteratively hashes the concatenated (unique) features to a new integer feature. Since the hash function is mapping randomly and uniformly to a 232-size space of integers, the ECFPs are often considered to be non-invertible However, there has been reverse-engineering methods in prior art that may deduce the molecular structure given revealed ECFPs which would jeopardize the sanctity of intellectual property of private companies and structure disclosure that would restrict individual scientists in a federated learning module.

Therefore some embodiments may feature a customized federated learning module that allows model training to be conducted securely on client machines without external access while still allowing the administrator to use the trained model.

Figure 13:
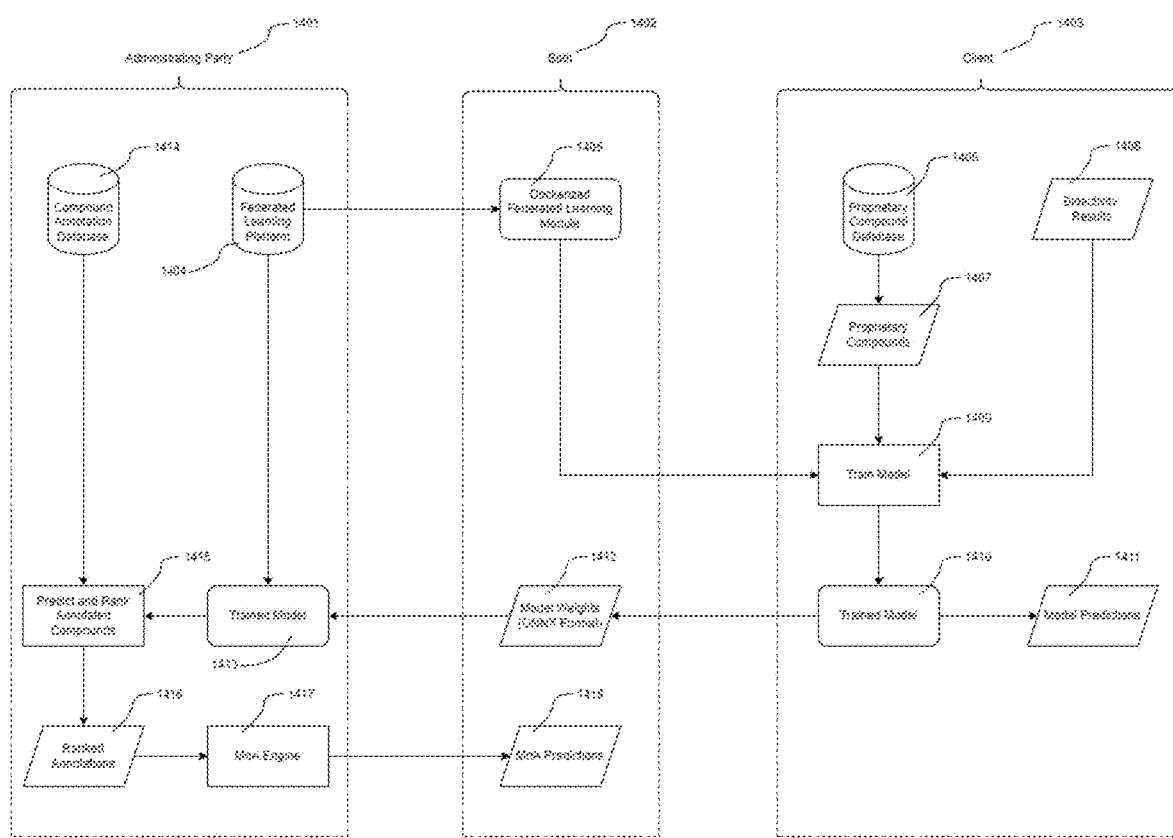
FIG. 13 is a flow diagram of an exemplary process for using parallel computing networks and associated API specifically for data preprocessing for biomedical predictive model creation over a cloud network.

FIG. 13 is related to information exchange process for federated learning models that ensures bi-directional data security.

The dashed box labeled 1401 shows all of the data the administrator has access to, the dashed box labeled 1403 shows all the data the client has access to, and the dashed box labeled 1402 shows all the data both parties have access to.

Starting at box 1404, a database stores the federated learning platform, some of which may be proprietary to the administrating party. From this database, a containerized federated learning module via Docker in 1405 can be extracted and shared among both parties.

Docker is a containerization platform which is used to package an application and all its dependencies together in the form of containers so to make sure that the application works seamlessly in any environment which can be in development or test or production.

In essence, containers share the same host kernel but are isolated from each other through private namespaces and resource control mechanisms at the OS level. Container-based virtualization provides a different level of abstraction in terms of virtualization and isolation when compared with hypervisors. Hypervisors use a lot of hardware which results in overhead in terms of virtualizing hardware and virtual device drivers.

Containers implement isolation of processes at the operating system level, thus avoiding such overhead. These containers run on top of the same shared operating system kernel of the underlying host machine and one or more processes can be run within each container.

There are several other advantages to utilizing Docker in addition to its promise to solve the privacy-preserving federated machine learning.

One advantage Docker offers is speed. The speed of Docker containers compared to a virtual machine is very fast. The time required to build a container is very fast because they are tiny and lightweight. Development, testing, and deployment can be done faster as containers are small. Containers can be pushed for testing once they have been built and then from there on to the production environment.

Another advantage Docker offers is portability. The applications that are built inside docker containers are extremely portable. These portable applications can easily be moved anywhere as a single element and their performance also remains the same.

Another advantage Dockers offers is density. Docker uses the resources that are available more efficiently because it does not use a hypervisor. This is the reason that more containers can be run on a single host as compared to virtual machines. Docker Containers have higher performance because of their high density and no overhead wastage of resources.

The client will have a secure database 1406 that stores information about proprietary compounds. The proprietary compounds data 1407 can be extracted from the database and, along with the federated learning module 1405 and empirical bioactivity results 1408, can be sent to module 1409 where a chemical structure-activity model is trained. The resulting trained model 1410 can be used to generate predictions 1411 that can stay internal to the client.

In order to keep the information about the proprietary compounds secure, the trained model is kept as an internal entity to the client, while the model weights in Open Neural Network Exchange (ONNX) format 1412 are shared with the administrating party.

ONNX is a set of tools used to better hangle storing, transferring and deploying model architectures and trained weights. Specifically, ONNX was designed to be cross platform, allowing models to be trained and deployed in different contexts. Although it was originally developed for neural networks, this set of tools has been expanded to cover tree-based models as well as which are used extensively in this process.

The administrating party can then use the model weights 1412 as well as the federated learning platform 1404 to create their own trained model 1413. In this way, the administrating party can gain insight from the client's model without compromising the security of the client's proprietary data.

The administrator can then use their trained model 1413 and their own compound annotation database 1414 to predict the phenotypic characteristics of compounds and rank the predictions 1415. The ranked annotations 1416 can then be processed through the mechanism of action engine 1417 to generate mechanism of action predictions 1418 that can be used by either party without compromising the security of any proprietary data.

Parallel computing may also enable that multiple devices be used simultaneously. For example, a set of network devices can be used to transmit various communications from a single user, or remote server may include a server stack. As another example, data may be processed as part of computing environment. Each communication within data transmission network may occur over one or more networks. Networks may include one or more of a variety of different types of networks, including a wireless network, a wired network, or a combination of a wired and wireless network. Examples of suitable networks include the Internet, a personal area network, a local area network (LAN), a wide area network (WAN), or a wireless local area network (WLAN).

Some aspects may utilize the Internet of Things (IoT), where things (e.g., machines, devices, phones, sensors) can be connected to networks and the data from these things can be collected and processed within the things and/or external to the things. For example, the IoT can include sensors in many different devices, and high value analytics can be applied to identify hidden relationships and drive increased efficiencies. This can apply to both big data analytics and real-time (e.g., ESP) analytics.

In data parallelism, the same machine learning model is trained on different processors by dividing the training data and sending each data division to a separate instance of the same machine learning algorithm. In model parallelism, different layers of one model can be trained on different processors, which is similar to the above example of parallelization of a mathematical sequential algorithm and is more complex than data parallelism. In this method, the ML algorithm itself is divided into smaller pieces by algorithmic parallelization and exposed to the same dataset. Some of the data retrieved from the database and even some of the results sent back to the user can also be stored in a caching engine.

This allows for future users to access common data for the completion of the same task and even to aid completion of similar tasks. Tasks that the user requests the parallel computing network to complete are sent to the task queue. The task queue can identify where there is any overlap for multiple users. If there is overlap, the tasks can be further divided so that each instance of overlap only needs to be completed once.

(12) Computer Systems for Implementing Various Embodiments

Figure 9:
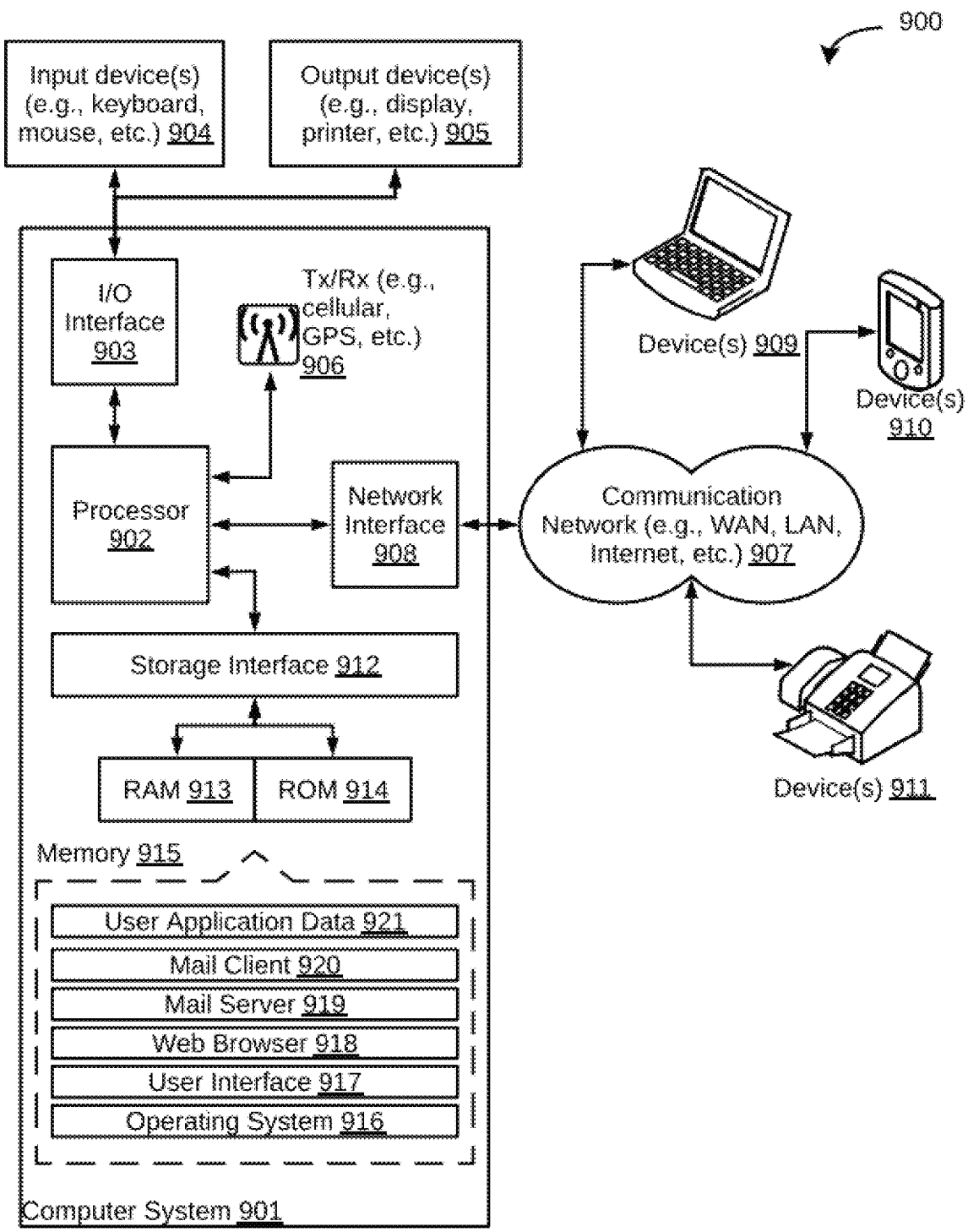
FIG. 9 is a block diagram of an exemplary computer system for implementing embodiments consistent with the present disclosure.

Referring now to FIG. 9, a block diagram of an exemplary computer system 901 for implementing embodiments consistent with the present disclosure is illustrated. Computer system 901 may include a central processing unit ("CPU" or "processor") 902. Processor 902 may include at least one data processor for executing program components for executing user- or system-generated requests. A user may include a person, a person using a device such as such as those included in this disclosure, or such a device itself. Processor 902 may include specialized processing units such as integrated system (bus) controllers, memory management control units, floating point units, graphics processing units, digital signal processing units, etc. Processor 902 may include a microprocessor, such as AMD® ATHLON® microprocessor, DURON® microprocessor OR OPTERON® microprocessor, ARM's application, embedded or secure processors, IBM® POWERPC®, INTEL'S CORE® processor, ITANIUM® processor, XEON® processor, CELERON® processor or other line of processors, etc. Processor 902 may be implemented using mainframe, distributed processor, multi-core, parallel, grid, or other architectures. Some embodiments may utilize embedded technologies like application-specific integrated circuits (ASICs), digital signal processors (DSPs), Field Programmable Gate Arrays (FPGAs), Graphical Processing Units (GPUs) (Nvidia, AMD, Asus, Intel, EVGA, and others), Tensor Processing Unites (Google), etc.

Processor 902 may be disposed in communication with one or more input/output (I/O) devices via an I/O interface 903. I/O interface 903 may employ communication protocols/methods such as, without limitation, audio, analog, digital, monoaural, RCA, stereo, IEEE-1394, serial bus, universal serial bus (USB), infrared, PS/2, BNC, coaxial, component, composite, digital visual interface (DVI), high-definition multimedia interface (HDMI), RF antennas, S-Video, VGA, IEEE 802. n/b/g/n/x, Bluetooth, cellular (e.g., code-division multiple access (CDMA), high-speed packet access (HSPA+), global system for mobile communications (GSM), long-term evolution (LTE), WiMax, or the like), etc.

Using I/O interface 903, computer system 901 may communicate with one or more I/O devices. For example, an input device 904 may be an antenna, keyboard, mouse, joystick, (infrared) remote control, camera, card reader, fax machine, dongle, biometric reader, microphone, touch screen, touchpad, trackball, sensor (e.g., accelerometer, light sensor, GPS, gyroscope, proximity sensor, or the like), stylus, scanner, storage device, transceiver, video device/ source, visors, etc. An output device 905 may be a printer, fax machine, video display (e.g., cathode ray tube (CRT), liquid crystal display (LCD), light-emitting diode (LED), plasma, or the like), audio speaker, etc. In some embodiments, a transceiver 906 may be disposed in connection with processor 902. Transceiver 906 may facilitate various types of wireless transmission or reception. For example, transceiver 906 may include an antenna operatively connected to a transceiver chip (e.g., TEXAS® INSTRUMENTS WILINK WL1283® transceiver, BROADCOM® BCM4SSOIUB8® transceiver, INFINEON TECHNOLOGIES® X-GOLD 618-PMB9800® transceiver, or the like), providing IEEE 802.11a/b/g/n, Bluetooth, FM, global positioning system (GPS), 2G/3G HSDPA/HSUPA communications, etc.

In some embodiments, processor 902 may be disposed in communication with a communication network 907 via a network interface 908. Network interface 908 may communicate with communication network 907. Network interface 616 may employ connection protocols including, without limitation, direct connect, Ethernet (e.g., twisted pair 50/500/5000 Base T), transmission control protocol/internet protocol (TCP/IP), token ring, IEEE 802.11a/b/g/n/x, etc. Communication network 907 may include, without limitation, a direct interconnection, local area network (LAN), wide area network (WAN), wireless network (e.g., using Wireless Application Protocol), the Internet, etc. Using network interface 908 and communication network 907, computer system 901 may communicate with devices 909, 910, and 911. These devices may include, without limitation, personal computer(s), server(s), fax machines, printers, scanners, various mobile devices such as cellular telephones, smartphones (e.g., APPLE® (PHONE® smartphone, BLACKBERRY® smartphone, ANDROID® based phones, etc.), tablet computers, eBook readers (AMAZON® KINDLE® ereader, NOOK® tablet computer, etc.), laptop computers, notebooks, gaming consoles (MICROSOFT® XBOX® gaming console, NINTENDO® DS® gaming console, SONY® PLAYSTATION® gaming console, etc.), or the like. In some embodiments, computer system 901 may itself embody one or more of these devices.

In some embodiments, processor 902 may be disposed in communication with one or more memory devices (e.g., RAM 626, ROM 628, etc.) via a storage interface 912. Storage interface 912 may connect to memory 915 including, without limitation, memory drives, removable disc drives, etc., employing connection protocols such as serial advanced technology attachment (SATA), integrated drive electronics (IDE), IEEE-1394, universal serial bus (USB), fiber channel, small computer systems interface (SCSI), etc. The memory drives may further include a drum, magnetic disc drive, magneto-optical drive, optical drive, redundant array of independent discs (RAID), solid-state memory devices, solid-state drives, etc.

Memory 915 may store a collection of program or database components, including, without limitation, an operating system 916, user interface application 917, web browser 918, mail server 919, mail client 920, user/application data 921 (e.g., any data variables or data records discussed in this disclosure), etc. Operating system 916 may facilitate resource management and operation of computer system 901. Examples of operating systems 916 include, without limitation, APPLE® MACINTOSH® OS X platform, UNIX platform, Unix-like system distributions (e.g., Berkeley Software Distribution (BSD), FreeBSD, NetBSD, OpenBSD, etc.), LINUX distributions (e.g., RED HAT®, UBUNTU®, KUBUNTU®, etc.), IBM® OS/2 platform, MICROSOFT® WINDOWS® platform (XP, Vista/7/8, etc.), APPLE® IOS® platform, GOOGLE® ANDROID® platform, BLACKBERRY® OS platform, or the like. User interface 917 may facilitate display, execution, interaction, manipulation, or operation of program components through textual or graphical facilities. For example, user interfaces may provide computer interaction interface elements on a display system operatively connected to computer system 901, such as cursors, icons, check boxes, menus, scrollers, windows, widgets, etc. Graphical user interfaces (GUIs) may be employed, including, without limitation, APPLE® Macintosh® operating systems' AQUA® platform, IBM® OS/2® platform, MICROSOFT® WINDOWS® platform (e.g., AERO® platform, METRO® platform, etc.), UNIX X-WINDOWS, web interface libraries (e.g., ACTIVEX® platform, JAVA® programming language, JAVASCRIPT® programming language, AJAX® programming language, HTML, ADOBE® FLASH® platform, etc.), or the like.

In some embodiments, computer system 901 may implement a web browser 918 stored program component. Web browser 918 may be a hypertext viewing application, such as MICROSOFT® INTERNET EXPLORER® web browser, GOOGLE® CHROME® web browser, MOZILLA® FIREFOX® web browser, APPLE® SAFARI® web browser, etc. Secure web browsing may be provided using HTTPS (secure hypertext transport protocol), secure sockets layer (SSL), Transport Layer Security (TLS), etc. Web browsers may utilize facilities such as AJAX, DHTML, ADOBE® FLASH® platform, JAVASCRIPT® programming language, JAVA® programming language, application programming interfaces (APIs), etc. In some embodiments, computer system 901 may implement a mail server 919 stored program component. Mail server 919 may be an Internet mail server such as MICROSOFT® EXCHANGE® mail server, or the like. Mail server 638 may utilize facilities such as ASP, ActiveX, ANSI C++/C #, MICROSOFT .NET® programming language, CGI scripts, JAVA® programming language, JAVASCRIPT® programming language, PERL® programming language, PHP® programming language, PYTHON® programming language, WebObjects, etc. Mail server 919 may utilize communication protocols such as internet message access protocol (IMAP), messaging application programming interface (MAPI), Microsoft Exchange, post office protocol (POP), simple mail transfer protocol (SMTP), or the like. In some embodiments, computer system 901 may implement a mail client 920 stored program component. Mail client 920 may be a mail viewing application, such as APPLE MAIL® mail client, MICROSOFT ENTOURAGE® mail client, MICROSOFT OUTLOOK® mail client, MOZILLA THUNDERBIRD® mail client, etc.

In some embodiments, computer system 901 may store user/application data 921, such as the data, variables, records, etc. as described in this disclosure. Such databases may be implemented as fault-tolerant, relational, scalable, secure databases such as ORACLE® database OR SYBASE® database. Alternatively, such databases may be implemented using standardized data structures, such as an array, hash, linked list, struct, structured text file (e.g., XML), table, or as object-oriented databases (e.g., using OBJECTSTORE® object database, POET® object database, ZOPE® object database, etc.). Such databases may be consolidated or distributed, sometimes among the various computer systems discussed above in this disclosure. It is to be understood that the structure and operation of the any computer or database component may be combined, consolidated, or distributed in any working combination.

It will be appreciated that, for clarity purposes, the above description has described embodiments of the invention with reference to different functional units and processors. However, it will be apparent that any suitable distribution of functionality between different functional units, processors or domains may be used without detracting from the invention. For example, functionality illustrated to be performed by separate processors or controllers may be performed by the same processor or controller. Hence, references to specific functional units are only to be seen as references to suitable means for providing the described functionality, rather than indicative of a strict logical or physical structure or organization.

As will be appreciated by those skilled in the art, the techniques described in the various embodiments discussed above are not routine, or conventional, or well understood in the art. The techniques discussed above provide for preprocessing biomedical data for a predictive model using an ML algorithm. The ML algorithm uses different permutations of preprocessing parameters to generate an optimized preprocessing algorithm. The preprocessing of biomedical data is implemented via an AI/ML-based framework for big data analytics of biomedical data. The AI/ML-based framework also provides for an iterative feature selection module, a capability for integration of various datasets, and a parallel computing network. Various datasets are integrated, and the features are then selected for the combined dataset. The feature selection is optimized by another ML algorithm. The parallel computing network allows a plurality of users to work together on a same input data and can also be used to implement containerized deployment to execute the analytics at a faster rate.

The specification has described a method and a system for preprocessing biomedical data for a predictive model. The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A method for reducing bias in a machine learning (ML) preprocessing algorithm in a healthcare context such that users can give data to said machine learning to produce a predictive result, the method comprising:
    obtaining raw data sets;
    generating preprocessing steps and bias correction parameters for multiple algorithms that will be applied to the raw data sets;
    training the multiple algorithms on obtained raw data sets with matching empirical results;
    iterating the multiple algorithms and bias correction parameters until there is a convergence of a model predicted data and empirical training data within a specified tolerance;
    assigning each algorithm of the multiple algorithms a score calculated based on a predictive power of each respective algorithm; and
    selecting one of the multiple algorithms having the highest score.

2. The method of claim 1, wherein the ML preprocessing algorithm trains with multiple heterogeneous datasets simultaneously.

3. The method of claim 1, wherein the ML preprocessing algorithm includes parameters for bias correction to homogenize datasets of same format and feature selection parameters to simultaneously consider and integrate datasets of different formats.

4. The method of claim 1, wherein each feature selection permutation on the combined dataset is measured by calculating the accuracy of predictive model quantity against the associated empirical quantities.

5. The method of claim 1, wherein the step of iterating algorithms feature at least one of COMBAT, robust scaling, regression, Bayes, mutual nearest neighbor or any other known batch effect correction algorithm.

6. The method of claim 1, wherein obtained raw data sets dimensions are reduced by principal component analysis and any dimension reduction strategy including UMAP and t-SNE.

7. The method of claim 1, wherein the data is one of Magnetic Resonance Imaging (MRI) data, functional Magnetic Resonance (fMRI) data, Electroencephalogram (EEG) data, Electrocardiogram (EKG/ECG) data, genetics data, protemics data, data from wearable devices, Electronic Health Record (EHR) data, Electronic Medical Record (EMR) data, Chemical structure data, Images (PNG, JPEG), including from pathology or other applications of microscopy, and other healthcare and medical research or healthcare related data.

8. The method of claim 1, wherein the operations further comprise:
    detecting a bias in the data, wherein the bias comprises at least one of a selection bias, a reporting bias, a recall bias, an exclusion bias, an information bias, or a statistical bias;
    determining if bias is a biological signal or not;
    applying a suitable algorithm to reduce bias.

9. The method of claim 8, wherein the data is one of Magnetic Resonance Imaging (MRI) data, functional Magnetic Resonance (fMRI) data, Electroencephalogram (EEG) data, Electrocardiogram (EKG/ECG) data, genetics data, protemics data, data from wearable devices, Electronic Health Record (EHR) data, Electronic Medical Record (EMR) data, Chemical structure data, Images (PNG, JPEG), including from pathology or other applications of microscopy, and other healthcare and medical research or healthcare related data.

* * * * *